(12) United States Patent
Chiu

(10) Patent No.: US 10,955,419 B2
(45) Date of Patent: Mar. 23, 2021

(54) METHODS AND SYSTEMS FOR ANALYSIS USING POLYMER DOTS

(71) Applicant: University of Washington, Seattle, WA (US)

(72) Inventor: Daniel T. Chiu, Seattle, WA (US)

(73) Assignee: University of Washington, Seattle, WA (US)

( * ) Notice: Subject to any disclaimer, the term of this patent is extended or adjusted under 35 U.S.C. 154(b) by 613 days.

(21) Appl. No.: 14/772,608

(22) PCT Filed: Mar. 5, 2014

(86) PCT No.: PCT/US2014/020930
§ 371 (c)(1),
(2) Date: Sep. 3, 2015

(87) PCT Pub. No.: WO2014/138312
PCT Pub. Date: Sep. 12, 2014

(65) Prior Publication Data
US 2016/0018405 A1 Jan. 21, 2016

Related U.S. Application Data

(60) Provisional application No. 61/773,044, filed on Mar. 5, 2013.

(51) Int. Cl.
*B82Y 15/00* (2011.01)
*G01N 33/58* (2006.01)
(Continued)

(52) U.S. Cl.
CPC ....... *G01N 33/588* (2013.01); *G01N 33/6803* (2013.01); *B82Y 15/00* (2013.01);
(Continued)

(58) Field of Classification Search
CPC ............. G01N 33/588; G01N 33/6803; G01N 2458/30; B82Y 40/00; B82Y 15/00; Y10S 977/774; Y10S 977/92
See application file for complete search history.

(56) References Cited

U.S. PATENT DOCUMENTS

2005/0037353 A1 2/2005 Zhang et al.
2009/0277791 A1 11/2009 Vu et al.
(Continued)

FOREIGN PATENT DOCUMENTS

CN 1030141 A 1/1989
CN 1639574 A 7/2005
(Continued)

OTHER PUBLICATIONS

Green et al., "A simple conjugated polymer nanoparticles as biological labels", Proc. R. Soc. A (2009) vol. 465, pp. 2751-2759 (Year: 2009).*
(Continued)

*Primary Examiner* — Tracy Vivlemore
*Assistant Examiner* — Nam P Nguyen
(74) *Attorney, Agent, or Firm* — Christensen O'Connor Johnson Kindness PLLC

(57) ABSTRACT

Methods, systems, compositions and kits are provided for the analysis of target molecules using chromophoric polymer dots conjugated to biomolecules. The use of chromophoric polymer dots improves detection sensitivity and stability when compared with existing techniques. In some aspects, methods, systems, and kits are provided for detecting a target protein using chromophoric polymer dots conjugated to biomolecules in a Western blot analysis. Related methods, systems, compositions and kits are also provided.

15 Claims, 5 Drawing Sheets

(51) Int. Cl.
*G01N 21/64* (2006.01)
*G01N 33/68* (2006.01)
*B82Y 40/00* (2011.01)

(52) U.S. Cl.
CPC .......... *B82Y 40/00* (2013.01); *G01N 2458/30* (2013.01); *Y10S 977/774* (2013.01); *Y10S 977/92* (2013.01)

(56) References Cited

U.S. PATENT DOCUMENTS

| | | | |
|---|---|---|---|
| 2009/0297448 | A1 | 12/2009 | Yan et al. |
| 2010/0098773 | A1* | 4/2010 | Hammer .............. A61K 9/0009 424/501 |
| 2012/0046191 | A1 | 2/2012 | Vu et al. |
| 2012/0282632 | A1 | 11/2012 | Chin et al. |

FOREIGN PATENT DOCUMENTS

| | | |
|---|---|---|
| WO | WO-2008133075 A1 | 11/2008 |
| WO | WO 2011/057295 A2 | 5/2011 |
| WO | WO 2012/054525 A2 | 4/2012 |
| WO | WO 2012/083235 A1 | 6/2012 |
| WO | 2012/122302 A3 | 9/2012 |
| WO | WO 2013/101902 A2 | 7/2013 |
| WO | WO 2014/153051 A1 | 9/2014 |
| WO | WO-2014138312 A1 | 9/2014 |
| WO | WO 2015/006714 A1 | 1/2015 |

OTHER PUBLICATIONS

Chan et al. (J. Am. Chem. Soc., 2012, vol. 134, pp. 7309-7312 and Supporting Information) (Year: 2012).*
JP 2015-561626 Office Action dated Feb. 1, 2018.
International search report and written opinion dated Jun. 9, 2014 for PCT/US2014/020930.
Ye, et al. A compact and highly fluorescent orange-emitting polymer dot for specific subcellular imaging. Chem Commun (Camb). Feb. 7, 2012;48(12):1778-80. doi: 10.1039/c2cc16486h. Epub Jan. 4, 2012.
CN 201480025609.2 Third Office Action dated Jan. 31, 2018.
Das, et al., Collapse of a Hydrophobic Polymer in a Mixture of Denaturants American Chemical Society, Langmuir, Mar. 21, 2013, 29, 4877-82.
CN 201480025609.2. Second Office action dated Jun 16, 2017.
European search report dated Aug. 17, 2016 for EP Application No. 14761091.
Wu, et al. Highly fluorescent semiconducting polymer dots for biology and medicine. Angew Chem Int Ed Engl. Mar. 11, 2013;52(11):3086-109. doi: 10.1002/anie.201205133. Epub Jan. 10, 2013.
Ye, et al. Ultrasensitive detection of proteins on western blots with semiconducting polymer dots. Macromolecular Rapid Communications. 2013; 34(9), 785-790.
Ye, et al. Ultrasensitive protein detection on dot blots and western blots with semiconducting polymer dots. Methods in Molecular Biology: Detection of Blotted Proteins. Springer New York, USA. Jan. 2015; Chapter 14, 1314:131-137.
Bakalova, et al., Quantum dot-based western blot technology for ultrasensitive detection of tracer proteins, Journal of the American Chemical Society, Jul. 2005, 127(26):9328-9329.
Bolt, et al., High-efficiency blotting of proteins of diverse sizes following sodium dodecyl sulfate-polyacrylamide gel electrophoresis, Analytical Biochemistry, May 1997, 247(2):185-192.
Chan, et al., Copper (II) and iron(II) ion sensing with semiconducting polymer dots, Chemical Communications, Epub Jan. 2011, 47(10):2820-22.
Chan, et al., Development of ultrabright semiconducting polymer dots for ratiometric pH sensing, Analytical Chemistry, Feb. 2011, 83(4):1448-55.
Chen, et al., Ultrasensitive detection of trace protein by Western blot based on POLY-quantum dot probes, Analytical Chemistry, Nov. 2009, 81(21):9194-9198.
Extended European search report dated Nov. 21, 2016 for EP Application No. 14761091.
Gilroy, et al., A simple, sensitive and selective quantum-dot-based western blot method for the simultaneous detection of multiple targets from cell lysates, Analytical and Bioanalytical Chemistry, Sep. 2010, 398(1):547-554.
Hawe, et al., Extrinsic fluorescent dyes as tools for protein characterization, Pharmaceutical Research, Jul. 2008, 25(7):1487-1499.
Kamaly, et al., Targeted polymeric therapeutic nanoparticles: design, development and clinical translation, Chemical Society Reviews, Apr. 2012, 41(7):2971-3010.
Kurien, et al., Western blotting, Methods, Apr. 2006, 38(4):283-293.
Liu, et al., Compact biocompatible quantum dots functionalized for cellular imaging, Journal of the American Chemical Society, Jan. 2008, 130(4):1274-84.
Ornberg, et al., Western blot analysis with quantum dot fluorescence technology: a sensitive and quantitative method for multiplexed proteomics, Jan. 2005, Nature Methods, Jan. 2005, 2(1):79-81.
Pu, et al., Fluorescent Single-Molecular Core—Shell Nanospheres of Hyperbranched Conjugated Polyelectrolyte for Live-Cell Imaging, Chemistry of Materials, Epub Aug. 2009, 21(16):3816-22.
Rahim, et al., Conjugated Polymer Nanoparticles for Two-Photon Imaging of Endothelial Cells in a Tissue Model, Advanced Materials, Sep. 2009, 21(34):3492-96.
Scholl, et al., Single particle quantum dot imaging achieves ultrasensitive detection capabilities for Western immunoblot analysis, Jun. 2009, ACS Nano, 3(6):1318-1328.
Vonarbourg, et al., Parameters influencing the stealthiness of colloidal drug delivery systems, Biomaterials, Aug. 2006, 27(24):4356-4373.
Wu, et al., Bioconjugation of ultrabright semiconducting polymer dots for specific cellular targeting, Journal of the American Chemical Society, Nov. 2010, 132(43):15410-15417.
Wu, et al., Conjugated polymer dots for multiphoton fluorescence imaging, Journal of the American Chemical Society, Oct. 2007, 129(43):12904-12905.
Wu, et al., Design of highly emissive polymer dot bioconjugates for in vivo tumor targeting, Angewandte Chemie International Edition, Apr. 2011, 50(15):3430-3434.
Wu, et al., Energy transfer mediated fluorescence from blended conjugated polymer nanoparticles, Journal of Physical Chemistry B, Jul. 2006, 110(29):14148-14154.
Wu, et al., Multicolor conjugated polymer dots for biological fluorescence imaging, ACS Nano, Nov. 2008, 2(11):2415-23.
Wu, et al., Ratiometric single-nanoparticle oxygen sensors for biological imaging, Angewandte Chemie International Edition, Mar. 2009, 48(15):2741-45.
Wu, et al., Swelling-controlled polymer phase and fluorescence properties of polyfluorene nanoparticles, Langmuir, Jul. 2008, 24(11):5855-5861.
Wu, et al., Ultrabright and bioorthogonal labeling of cellular targets using semiconducting polymer dots and click chemistry, Angewandte Chemie International Edition, Dec. 2010, 49(49):9436-9440.
Ye, et al., Ratiometric temperature sensing with semiconducting polymer dots, Journal of the American Chemical Society, Jun. 2011, 133(21):8146-49.
Yu, et al., Nanoscale 3D tracking with conjugated polymer nanoparticles, Journal of the American Chemical Society, Dec. 2009, 131(51):18410-414.
Yu, et al., Stable functionalization of small semiconducting polymer dots via covalent cross-linking and their application for specific cellular imaging, Advanced Materials, Jul. 2012, 24(26):3498-3504.
Zhang, et al., Importance of having low-density functional groups for generating high-performance semiconducting polymer dots, ACS Nano, (Jun. 2012, 6(6):5429-5439.
"EP 14761091.9 Office Action dated Apr. 11, 2018".
"EP 14761091.9 Office Action dated Mar. 21, 2018".
Firer et al. Efficient elution of functional proteins in affinity chromatography, Journal of Biochemical and Biophysical Methods, Oct. 30, 2001, 49:433-442.

(56) References Cited

OTHER PUBLICATIONS

Rong et al., "Multicolor Fluorescent Semiconducting Polymer Dots with Narrow Emissions and High Brightness," American Chemical Society, vol. 7, No. 1, Jan. 1, 2013, 9 pages.
Extended European Search Report, dated Jun. 17, 2019, issued in corresponding European Patent Application No. 19171956.6, filed Mar. 5, 2014, 13 pages.
Giridharagopal, R. and Ginger, D.S., "Characterizing Morphology in Bulk Heterojunction Organic Photovoltaic Systems," J. Phys. Chem. Lett., 1:1160-1169, 2010.
Ginger, D.S. and Greenham, N.C., "Photoinduced electron transfer from conjugated polymers to CdSe nanocrystals," Phys. Rev. B, 59(16):10622-10629, Apr. 15, 1999.
Ginger, D.S. and Greenham, N.C., "Charge Separation in Conjugated-Polymer/Nanocrystal Blends," Synthetic Metals, 101:425-428, 1999.
Groves, C. et al., "Heterogeneity in Polymer Solar Cells: Local Morphology and Performance in Organic Photovoltaics Studied with Scanning Probe Microscopy," Accounts of Chemical Research, 43(5):612-620, May 2010.
Hoppe, H. et al., "Nanoscale Morphology of Conjugated Polymer/Fullerene-Based Bulk-Heterojunction Solar Cells," Adv. Fund. Mater., 14(10:1005-1011, Oct. 2004.
Moule, A.J. and Meerholz, K., "Morphology Control in Solution-Processed Bulk-Heterojunction Solar Cell Mixtures," Adv. Fund. Mater., 19:3028-3036, 2009.

\* cited by examiner

METHODS AND SYSTEMS FOR ANALYSIS USING POLYMER DOTS

CROSS-REFERENCE

This application is a U.S. National Phase Application under 35 U.S.C. § 371 of International Application No. PCT/US2014/020930, filed Mar. 5, 2014, which claims the benefit of U.S. Provisional Application No. 61/773,044, filed Mar. 5, 2013, which application is incorporated herein by reference in its entirety for all purposes.

STATEMENT AS TO FEDERALLY SPONSORED RESEARCH

This invention was made with the support of the United States government under Contract number GM085485 by The National Institutes of Health, and Contract number CHE-0924320 by the National Science Foundation.

BACKGROUND

Western blotting is a widely used laboratory technique for protein analysis. In this technique, proteins are separated by sodium dodecyl sulfate-polyacrylamide gel electrophoresis (SDS-PAGE) and then transferred onto a hydrophobic membrane; the proteins are later visualized using various labelling procedures.

The traditional imaging method of chemiluminescence is based on protein labelling with horseradish peroxidase. Fluorescence detection has recently gained popularity because of its increased sensitivity and multiplex capability. However, fluorescent dyes for use with Western blotting tend to suffer from rapid photobleaching, which reduces the sensitivity of repetitive blot imaging. Quantum dots (Qdots) are an alternative source of fluorescence visualization that can be used for applications in Western blot analysis. However, techniques with quantum dots can require a somewhat complicated setup and analysis, which are not readily available in most biochemistry laboratories.

Thus, there is a need for improved techniques for visualizing proteins and peptides as part of Western blot analyses.

SUMMARY

In some aspects, the present invention provides methods and systems for analysis using polymer dots (or "Pdots"). In certain aspects, the present invention provides compositions of polymer dots for detecting proteins, including but not limited to Western blot analysis. The present invention also provides kits that can include polymer dots and, in some embodiments, a blocking agent suitable for Western blot analysis using polymer dots. The blocking agent can be used, e.g., to modify non-specific adsorption/interaction in applying polymer dots to Western blot analysis. The present disclosure also provides systems for analyzing protein or peptide samples using the Pdots.

In various aspects, the present disclosure provides methods for performing Western blot analysis, the method comprising: separating proteins with a gel; transferring the separated proteins to a membrane; contacting the membrane having the separated proteins with a solution comprising a polymer dot conjugated to a biomolecule specific to at least some of the separated proteins; and detecting at least one signal from the polymer dots, the at least one signal corresponding to the separated proteins In various aspects, the present disclosure provides methods for detecting proteins or peptides, the method comprising: separating the proteins or peptides from a mixture; contacting the separated proteins or peptides with a solution comprising a polymer dot conjugated to a biomolecule specific to at least some of the separated proteins or peptides; and detecting at least one signal from the polymer dots, the at least one signal corresponding to the separated proteins or peptides.

In various aspects, the present disclosure provides compositions comprising conjugated polymer dots for Western blot analysis and kits comprising the composition.

In various aspects, the present disclosure provides kits for performing Western blot analysis, the kit comprising polymer dots, a conjugation biomolecule, and a blocking agent.

In various aspects, the present disclosure provides systems for assaying a protein or peptide, the system comprising: a polymer dot conjugated to a biomolecule; a protein or peptide separation platform; a source of electromagnetic radiation; a detector; and a computer comprising a memory device with executable instructions stored thereon, the instructions when executed by the processor cause the processor to: operate the detector to acquire an image, store the image, and analyze the image.

In various aspects, the present disclosure provides systems for performing Western blot analysis, the system comprising: a polymer dot conjugated to a biomolecule; a gel; an electrophoresis platform; a source of electromagnetic radiation; a detector; and a computer comprising a memory device with executable instructions stored thereon, the instructions when executed by the processor cause the processor to: operate the detector to acquire an image, store the image, and analyze the image.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

DETAILED DESCRIPTION

Figure 1:
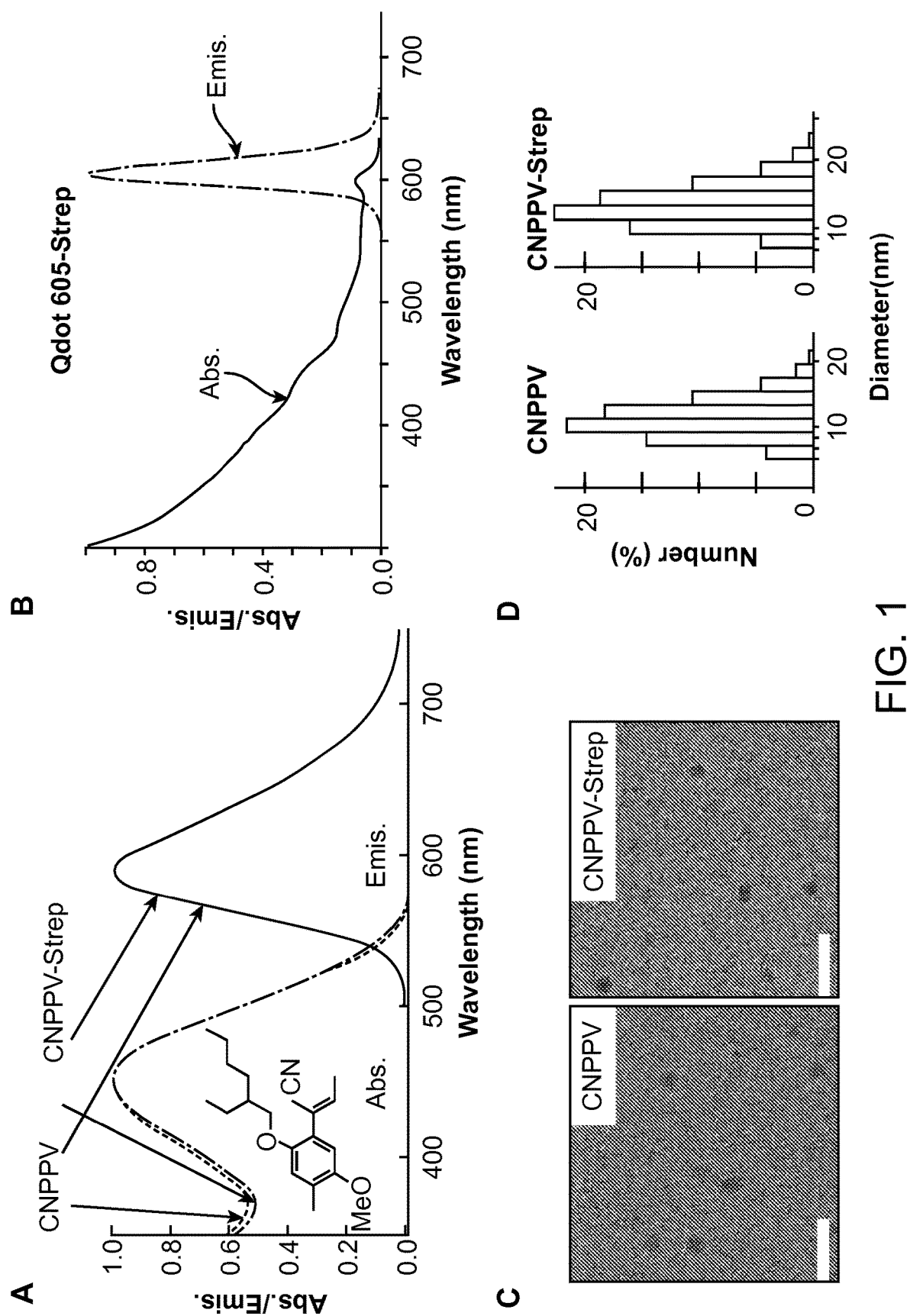
FIG. 1A shows a structure of CN-PPV polymer and the absorption (dashed) and emission (solid) spectra of CN-PPV Pdot and CN-PPV Pdot-streptavidin conjugate (CNPPV-Strep) in a 0.1% polyethylene glycol (PEG) 20 mM HEPES buffer.
FIG. 1B shows an absorption and emission spectra of Qdot 605-streptavidin conjugate from Invitrogen.
FIG. 1C shows an example TEM image of CN-PPV Pdot and CN-PPV-streptavidin Pdot; scale bars represent 50 nm in length.
FIG. 1D shows example dynamic light scattering measurements of both CN-PPV and CN-PPV-streptavidin Pdots.

The present invention provides methods, compositions, kits and systems for analysis using polymer dots. In various aspects, the present disclosure provides methods, compositions, and kits for performing Western blot analysis of proteins.

In some aspects of the present disclosure, methods, systems, compositions and kits are provided for detecting and analyzing target molecules using chromophoric polymer dots conjugated to biomolecules. The use of polymer dots offers improved detection sensitivity and stability compared with existing techniques.

As used herein, the term "alkyl" refers to a straight or branched, saturated, aliphatic radical having the number of carbon atoms indicated. For example, $C_1$-$C_6$ alkyl includes, but is not limited to, methyl, ethyl, propyl, isopropyl, butyl, isobutyl, sec-butyl, tert-butyl, pentyl, isopentyl, hexyl, etc. Other alkyl groups include, but are not limited to heptyl, octyl, nonyl, decyl, etc. Alkyl can include any number of carbons, such as 1-2, 1-3, 1-4, 1-5, 1-6, 1-7, 1-8, 1-9, 1-10, 2-3, 2-4, 2-5, 2-6, 3-4, 3-5, 3-6, 4-5, 4-6 and 5-6. The alkyl group is typically monovalent, but can be divalent, such as when the alkyl group links two moieties together. As used herein, the term "heteroalkyl" refers to a straight or branched, saturated, aliphatic radical of carbon atoms, where at least one of the carbon atoms is replaced with a heteroatom, such as N, O or S. Additional heteroatoms can also be useful, including, but not limited to, B, Al, Si and P.

The term "lower" referred to above and hereinafter in connection with organic radicals or compounds respectively defines a compound or radical which can be branched or unbranched with up to and including 7, preferably up to and including 4 and (as unbranched) one or two carbon atoms.

As used herein, the term "alkylene" refers to an alkyl group, as defined above, linking at least two other groups, i.e., a divalent hydrocarbon radical. The two moieties linked to the alkylene can be linked to the same atom or different atoms of the alkylene. For instance, a straight chain alkylene can be the bivalent radical of —$(CH_2)_n$—, where n is 1, 2, 3, 4, 5 or 6. Alkylene groups include, but are not limited to, methylene, ethylene, propylene, isopropylene, butylene, isobutylene, sec-butylene, pentylene and hexylene.

The groups described herein can be substituted or unsubstituted. Substituents for the alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) can be a variety of groups, such as alkyl, aryl, cyano (CN), amino, sulfide, aldehyde, ester, ether, acid, hydroxyl or halide. Substituents can be a reactive group, such as but not limited to chloro, bromo, iodo, hydroxyl, or amino. Suitable substituents can be selected from: —OR', =O, =NR', =N—OR', —NR'R", —SR', -halogen, —SiR'R"R'", —OC(O)R', —C(O)R', —CO$_2$R', —CONR'R", —OC(O)NR'R", —NR"C(O)R', —NR'—C(O)NR"R'", —NR"C(O)$_2$R', —NH—C(NH$_2$)=NH, —NR'C(NH$_2$)=NH, —NH—C(NH$_2$)=NR', —S(O)R', —S(O)$_2$R', —S(O)$_2$NR'R", —CN and —NO$_2$ in a number ranging from zero to (2m'+1), where m' is the total number of carbon atoms in such radical. R', R" and R'" each independently refer to hydrogen, unsubstituted ($C_1$-$C_8$)alkyl and heteroalkyl, unsubstituted aryl, alkoxy or thioalkoxy groups, or aryl-($C_1$-$C_4$)alkyl groups. When R' and R" are attached to the same nitrogen atom, they can be combined with the nitrogen atom to form a 5-, 6-, or 7-membered ring. For example, —NR'R" is meant to include 1-pyrrolidinyl and 4-morpholinyl. From the above discussion of substituents, one of skill in the art will understand that the term "alkyl" is meant to include groups such as haloalkyl (e.g., —CF$_3$ and —CH$_2$CF$_3$) and acyl (e.g., —C(O)CH$_3$, —C(O)CF$_3$, —C(O)CH$_2$OCH$_3$, and the like).

As used herein, the term "alkoxy" refers to an alkyl group having an oxygen atom that either connects the alkoxy group to the point of attachment or is linked to two carbons of the alkoxy group. Alkoxy groups include, for example, methoxy, ethoxy, propoxy, iso-propoxy, butoxy, 2-butoxy, iso-butoxy, sec-butoxy, tert-butoxy, pentoxy, hexoxy, etc. The alkoxy groups can be further substituted with a variety of substituents described within. For example, the alkoxy groups can be substituted with halogens to form a "haloalkoxy" group.

As used herein, the term "alkenyl" refers to either a straight chain or branched hydrocarbon of 2 to 6 carbon atoms, having at least one double bond. Examples of alkenyl groups include, but are not limited to, vinyl, propenyl, isopropenyl, 1-butenyl, 2-butenyl, isobutenyl, butadienyl, 1-pentenyl, 2-pentenyl, isopentenyl, 1,3-pentadienyl, 1,4-pentadienyl, 1-hexenyl, 2-hexenyl, 3-hexenyl, 1,3-hexadienyl, 1,4-hexadienyl, 1,5-hexadienyl, 2,4-hexadienyl, or 1,3,5-hexatrienyl.

As used herein, the term "alkenylene" refers to an alkenyl group, as defined above, linking at least two other groups, i.e., a divalent hydrocarbon radical. The two moieties linked to the alkenylene can be linked to the same atom or different atoms of the alkenylene. Alkenylene groups include, but are not limited to, ethenylene, propenylene, isopropenylene, butenylene, isobutenylene, sec-butenylene, pentenylene and hexenylene.

As used herein, the term "alkynyl" refers to either a straight chain or branched hydrocarbon of 2 to 6 carbon atoms, having at least one triple bond. Examples of alkynyl groups include, but are not limited to, acetylenyl, propynyl, 1-butynyl, 2-butynyl, isobutynyl, sec-butynyl, butadiynyl, 1-pentynyl, 2-pentynyl, isopentynyl, 1,3-pentadiynyl, 1,4-pentadiynyl, 1-hexynyl, 2-hexynyl, 3-hexynyl, 1,3-hexadiynyl, 1,4-hexadiynyl, 1,5-hexadiynyl, 2,4-hexadiynyl, or 1,3,5-hexatriynyl.

As used herein, the term "alkynylene" refers to an alkynyl group, as defined above, linking at least two other groups, i.e., a divalent hydrocarbon radical. The two moieties linked to the alkynylene can be linked to the same atom or different atoms of the alkynylene. Alkynylene groups include, but are not limited to, ethynylene, propynylene, isopropynylene, butynylene, sec-butynylene, pentynylene and hexynylene.

As used herein, the term "alkyl amine" refers to an alkyl groups as defined within, having one or more amino groups. The amino groups can be primary, secondary or tertiary. The alkyl amine can be further substituted with a hydroxy group. Alkyl amines can include, but are not limited to, ethyl amine, propyl amine, isopropyl amine, ethylene diamine and ethanolamine. The amino group can link the alkyl amine to the point of attachment with the rest of the compound, be at the omega position of the alkyl group, or link together at least two carbon atoms of the alkyl group.

As used herein, the term "halogen" or "halide" refers to fluorine, chlorine, bromine and iodine. As used herein, the term "haloalkyl" refers to alkyl as defined above where some or all of the hydrogen atoms are substituted with halogen atoms. Halogen (halo) preferably represents chloro or fluoro, but may also be bromo or iodo. As used herein, the term "halo-alkoxy" refers to an alkoxy group having at least one halogen. Halo-alkoxy is as defined for alkoxy where some or all of the hydrogen atoms are substituted with halogen atoms. The alkoxy groups can be substituted with 1, 2, 3, or more halogens. When all the hydrogens are replaced with a halogen, for example by fluorine, the compounds are per-substituted, for example, perfluorinated. Halo-alkoxy includes, but is not limited to, trifluoromethoxy, 2,2,2-trifluoroethoxy, perfluoroethoxy, and the like.

As used herein, the term "cycloalkyl" refers to a saturated or partially unsaturated, monocyclic, fused bicyclic or bridged polycyclic ring assembly containing from 3 to 12 ring atoms, or the number of atoms indicated. Monocyclic rings include, for example, cyclopropyl, cyclobutyl, cyclopentyl, cyclohexyl, and cyclooctyl. Bicyclic and polycyclic rings include, for example, norbornane, decahydronaphthalene and adamantane. For example, $C_{3-8}$cycloalkyl includes cyclopropyl, cyclobutyl, cyclopentyl, cyclohexyl, cyclooctyl, and norbornane.

As used herein, the term "cycloalkylene" refers to a cycloalkyl group, as defined above, linking at least two other groups, i.e., a divalent hydrocarbon radical. The two moieties linked to the cycloalkylene can be linked to the same atom or different atoms of the cycloalkylene. Cycloalkylene groups include, but are not limited to, cyclopropylene, cyclobutylene, cyclopentylene, cyclohexylene, and cyclooctylene.

As used herein, the term "heterocycloalkyl" refers to a ring system having from 3 ring members to about 20 ring members and from 1 to about 5 heteroatoms such as N, O and S. Additional heteroatoms can also be useful, including, but not limited to, B, Al, Si and P. The heteroatoms can also be oxidized, such as, but not limited to, —S(O)— and —S(O)$_2$7.

As used herein, the term "heterocycloalkylene" refers to a heterocycloalkyl group, as defined above, linking at least two other groups. The two moieties linked to the heterocycloalkylene can be linked to the same atom or different atoms of the heterocycloalkylene.

As used herein, the term "aryl" refers to a monocyclic or fused bicyclic, tricyclic or greater, aromatic ring assembly containing 6 to 16 ring carbon atoms. For example, aryl may be phenyl, benzyl, azulenyl or naphthyl. "Arylene" means a divalent radical derived from an aryl group. Aryl groups can be mono-, di- or tri-substituted by one, two or three radicals selected from alkyl, alkoxy, aryl, hydroxy, halogen, cyano, amino, amino-alkyl, trifluoromethyl, alkylenedioxy and oxy-$C_2$-$C_3$-alkylene; all of which are optionally further substituted, for instance as hereinbefore defined; or 1- or 2-naphthyl; or 1- or 2-phenanthrenyl. Alkylenedioxy is a divalent substitute attached to two adjacent carbon atoms of phenyl, e.g. methylenedioxy or ethylenedioxy. Oxy-$C_2$-$C_3$-alkylene is also a divalent substituent attached to two adjacent carbon atoms of phenyl, e.g. oxyethylene or oxypropylene. An example for oxy-$C_2$-$C_3$-alkylene-phenyl is 2,3-dihydrobenzofuran-5-yl.

Aryl groups can include, but are not limited to, naphthyl, phenyl or phenyl mono- or disubstituted by alkoxy, phenyl, halogen, alkyl or trifluoromethyl, phenyl or phenyl-mono- or disubstituted by alkoxy, halogen or trifluoromethyl, and in particular phenyl.

As used herein, the term "arylene" refers to an aryl group, as defined above, linking at least two other groups. The two moieties linked to the arylene are linked to different atoms of the arylene. Arylene groups include, but are not limited to, phenylene.

As used herein, the terms "alkoxy-aryl" or "aryloxy" refers to an aryl group, as defined above, where one of the moieties linked to the aryl is linked through an oxygen atom. Alkoxy-aryl groups include, but are not limited to, phenoxy ($C_6H_5O$—). The present invention also includes alkoxy-heteroaryl or heteroaryloxy groups.

As used herein, the term "heteroaryl" refers to a monocyclic or fused bicyclic or tricyclic aromatic ring assembly containing 5 to 16 ring atoms, where from 1 to 4 of the ring atoms are a heteroatom each N, O or S. For example, heteroaryl includes pyridyl, indolyl, indazolyl, quinoxalinyl, quinolinyl, isoquinolinyl, benzothienyl, benzofuranyl, furanyl, pyrrolyl, thiazolyl, benzothiazolyl, oxazolyl, isoxazolyl, triazolyl, tetrazolyl, pyrazolyl, imidazolyl, thienyl, or any other radicals substituted, especially mono- or di-substituted, by e.g. alkyl, nitro or halogen. Suitable groups for the present invention can also include heteroarylene and heterarylene-oxy groups similar to the description above for arylene and arylene-oxy groups.

Similarly, aryl and heteroaryl groups described herein can be substituted or unsubstituted. Substituents for the aryl and heteroaryl groups are varied, such as alkyl, aryl, CN, amino, sulfide, aldehyde, ester, ether, acid, hydroxyl or halide. Substituents can be a reactive group, such as but not limited to chloro, bromo, iodo, hydroxyl, or amino. Substituents can be selected from: -halogen, —OR', —OC(O)R', —NR'R", —SR', —R', —CN, —NO$_2$, —CO$_2$R', —CONR'R", —C(O)R', —OC(O)NR'R", —NR"C(O)R', —NR"C(O)$_2$R', —NR'—C(O)NR"R'", —NH—C(NH$_2$)=NH, —NR'C(NH$_2$)=NH, —NH—C(NH$_2$)=NR', —S(O)R', —S(O)$_2$R', —S(O)$_2$NR'R", —N$_3$, —CH(Ph)$_2$, in a number ranging from zero to the total number of open valences on the aromatic ring system; and where R', R" and R'" are independently selected from hydrogen, ($C_1$-$C_8$)alkyl and heteroalkyl, unsubstituted aryl and heteroaryl, (unsubstituted aryl)-($C_1$-$C_4$)alkyl, and (unsubstituted aryl)oxy-($C_1$-$C_4$)alkyl.

As used herein, the term "alkyl-aryl" refers to a radical having an alkyl component and an aryl component, where the alkyl component links the aryl component to the point of attachment. The alkyl component is as defined above, except that the alkyl component is at least divalent in order to link to the aryl component and to the point of attachment. In some instances, the alkyl component can be absent. The aryl component is as defined above. Examples of alkyl-aryl groups include, but are not limited to, benzyl. The present invention also includes alkyl-heteroaryl groups.

As used herein, the term "alkenyl-aryl" refers to a radical having both an alkenyl component and an aryl component, where the alkenyl component links the aryl component to the point of attachment. The alkenyl component is as defined above, except that the alkenyl component is at least divalent in order to link to the aryl component and to the point of attachment. The aryl component is as defined above. Examples of alkenyl-aryl include ethenyl-phenyl, among others. The present invention also includes alkenyl-heteroaryl groups.

As used herein, the term "alkynyl-aryl" refers to a radical having both an alkynyl component and a aryl component, where the alkynyl component links the aryl component to the point of attachment. The alkynyl component is as defined above, except that the alkynyl component is at least divalent in order to link to the aryl component and to the point of attachment. The aryl component is as defined above. Examples of alkynyl-aryl include ethynyl-phenyl, among others. The present invention also includes alkynyl-heteroaryl groups.

Chromophoric Polymer Dots

The present disclosure provides methods, systems, compositions and kits comprising chromophoric polymer dots (Pdots) for analyzing proteins and peptides. Pdots have superior optical properties making them particularly useful for the detection of proteins and other biological molecules.

Polymer dots (Pdots) have a number of advantages for use as detection agents. Pdots are fluorescent, polymer-based particles that can adopt a variety of configurations, including but not limited to, a monolithic polymer dot having a uniform, homogenous composition or a polymer dot having a distinct core and cap structure. Pdots can be made up of a single polymer or can comprise blends of polymers.

As used herein, the terms "polymer dot," "chromophoric polymer dot," "fluorescent polymer dot," "chromophoric nanoparticle" and "Pdot" are used interchangeably to refer to structures comprising one or more polymers (e.g., semiconducting polymers) that have been collapsed into a stable sub-micron-sized particle. The term "chromophoric polymer" refers to a polymer in which at least a portion of the polymer comprises a chromophoric unit that absorbs certain wavelengths of light ranging from UV to near infrared spectra. Chromophoric polymers according to the present disclosure may be or may not be emissive.

Polymer dots according to the present disclosure can comprise any suitable polymer subunit or subunits that enable the detection of proteins or peptides, and in particular, proteins.

As used herein, the term "polymer" refers to a molecule composed of at least two repeating structural units typically connected by covalent chemical bonds. The repeating structural unit can be one type of monomer, and the resulting polymer is a homopolymer. In some aspects, the polymers can include two different types of monomers, or three different types of monomers, or more types of monomers. One of ordinary skill in the art will appreciate that the different types of monomers can be distributed along a polymer chain in a variety of ways. For example, three different types of monomers can be randomly distributed along the polymer. It will similarly be appreciated that the distribution of monomers along the polymer can be represented in different ways.

The present disclosure provides Pdots that are semiconducting, non-semiconducting, or a combination thereof. Any polymer composition can be used according to the present disclosure so long as it is suitable for detecting proteins and peptides, such as for example, in the course of Western blot analysis.

The present disclosure provides for Pdots having desirable surface chemistry and optical properties, making them particularly well suited for the detection of proteins according to the present methods. The optical properties and degree of functionalization for a population of Pdots can be adjusted during production of the Pdots. In particular, the attributes of the Pdots can be adjusted as needed in order to tune a variety of photophysical properties (e.g., absorbance, emission brightness and/or the color of emission). In certain aspects, the polymer dots provide unexpected brightness and/or photostability. Notably, in some instances, quenching of fluorescence is not increased due to particle formation. Furthermore, low, discrete numbers of functional groups on the surface of the polymer dots can reduce non-specific absorption of the Pdots to biologically relevant molecules and/or cells. It will be appreciated that polymer dots having high brightness and specific binding capabilities provide important aspects to furthering areas of imaging and detection techniques for studying chemical and biological systems.

The chromophoric polymer dots used herein can be formed by any method known in the art for collapsing polymers, including without limitation, methods relying on precipitation, methods relying on the formation of emulsions (e.g., mini or micro emulsion), and methods relying on condensation.

In some aspects, Pdots can be formed by precipitation. This technique involves the rapid addition (e.g., facilitated by sonication or vigorous stirring) of a dilute chromophoric polymer solution (e.g., chromophoric polymer dissolved in an organic solvent) into an excess volume of non-solvent (but miscible with the organic solvent), such as water or another physiologically relevant aqueous solution. For example, in some of the procedures described herein, the chromophoric polymer can be first dissolved into an organic solvent where the solubility is good (good solvent), such as THF (tetrahydrofuran), after which the dissolved polymer in THF is added to an excess volume of water or buffer solution, which is a poor solvent for the hydrophobic chromophoric polymers but which is miscible with the good solvent (THF). The resulting mixture is sonicated or vigorously stirred to assist the formation of chromophoric polymer dots, then the organic solvent is removed to leave behind well dispersed chromophoric nanoparticles. In using this procedure, the chromophoric polymer should be sufficiently hydrophobic to dissolve into the organic solvent (e.g., THF). The introduction of a high density of hydrophilic functional groups on side chains for coupling to biomolecules or high density of hydrophilic side chains will make the resulting polymer, in a fashion similar or identical to the behavior of polyelectrolytes, insoluble or poorly soluble in an organic solvent (e.g., THF). In some aspects, methods, systems, compositions and kits are provided for the use of Pdots formed by other methods, including but not limited to various methods based on emulsions (e.g., mini or micro emulsion) or precipitations or condensations. Other polymers having hydrophobic functional groups can also be employed, in which the hydrophobic functional groups do not affect the collapse and stability of the chromophoric polymer dot. The hydrophobic functional groups on the surface of the nanoparticles can then be converted to hydrophilic functional groups (e.g., by post-functionalization) for bioconjugation or directly link the hydrophobic functional groups to biomolecules. This latter approach can work particularly well using functional groups that are both hydrophobic and clickable (i.e., chemical reactions that fall within the framework of click chemistry), including but not limited to alkyne, strained alkyne, azide, diene, alkene, cyclooctyne, and phosphine groups.

In some aspects, methods, systems, compositions and kits are provided for the use of functionalized Pdots that have been modified to form a single-molecule polymer dot that can be monovalent, bivalent, or multivalent. The modification is to remove some polymer molecules from the dot, but leave only one molecule that can have just one functional group, two or more functional groups. In one embodiment, an engineered surface can be used to facilitate the modification. The engineered surface can have certain functional groups such as aldehyde, alkene, alkyl, alkyne, strained alkyne, amino, azido, carbonyl, carboxyl, cyano, cyclooctyne, dieno, ester, succinimidyl ester, haloalkyl, hydroxyl, imido, ketone, maleimido, mercapto, phosphate, phosphine, sulfate, sulfonate, substituted derivatives thereof, and combinations thereof. In general, any other functional groups that are suitable for bioconjugation can be used. Such functional groups could be found by one of ordinary skill in the art, for example in Bioconjugate Techniques (Academic Press, New York, 1996 or later versions). The surface can be a flat surface such as a coverslip or a curved surface from any particles. The surfaces can be silica, metal, semiconducting, silicon, and different polymer surfaces. The functionalized multi-molecule chromophoric polymer dot described above is attached to the surface by only one chromophoric polymer molecule via any stable physical or chemical association. All the free molecules (except the one associated with the surface) in the chromophoric polymer dot can be removed, such as by washing the surface with an organic solvent, so that only the molecule associated with the surface is retained. Then the single-molecule chromophoric dot can be released from the surface by any physical or chemical methods. The resulting single-molecule dot could be monovalent, bivalent, or multivalent, depending on the number of functional groups in the original polymer molecule.

A number of semiconducting polymers are suitable for use according to the present disclosure. Semiconducting polymers have been developed with emission wavelengths ranging from UV to infrared, including the entire visible spectrum. In various aspects, methods, systems, compositions and kits are provided for the use of semiconducting polymers, including but not limited to: polyfluorene polymers including but not limited to poly(9,9-dihexylfluorenyl-2,7-diyl) (PDHF) and poly(9,9-dioctylfluorenyl-2,7-diyl) (PFO); fluorene-based copolymers, including but not limited to, poly[{9,9-dioctyl-2,7-divinylene-fluorenylene}-alt-co-12-methoxy-5-{2-ethylhexyloxy)-1,4-phenylene}] (PFPV), poly[(9,9-dioctylfluorenyl-2,7-diyl)-co-(1,4-benzo-{2,1,3}-thiadiazole)] (PFBT), poly[(9,9-dioctylfluorenyl-2,7-diyl)-co-(4,7-Di-2-thienyl-2,1,3-benzothiadiazole)] (PFTBT), and poly[(9,9-dioctylfluorenyl-2,7-diyl)-co-(4,7-Di-2-thienyl-2,1,3-benzothiadiazole)] (PF-0.1TBT); phenylene vinylene polymers, including but not limited to, poly[2-methoxy-5-(2-ethylhexyloxy)-1,4-phenylenevinylene] (MEH-PPV) and poly[2-methoxy-5-(2-ethylhexyloxy)-1,4-(1-cyanovinylene-1,4-phenylene)] (CN-PPV); phenylene ethynylene polymers, including but not limited to, poly(2,5-di(3',7'-dimethyloctyl)phenylene-1,4-ethynylene (PPE). In some aspects, Pdots can be used that contain a polystyrene-based, comb-like polymer. Non-limiting examples of polystyrene based comb-like polymers include, polystyrene graft acrylic acid, polystyrene graft ethylene oxide, polystyrene graft butyl alcohol, and the like.

In some aspects, Pdots can be used that contain poly (methyl methacrylate) based comb-like polymers. Non-limiting examples of poly(methyl methacrylate) based comb-like polymers include, poly(methyl methacrylate) graft acrylic acid, poly(methyl methacrylate) graft ethylene oxide, and the like.

In some aspects, Pdots can be used that contain a comb-like polymer comprising carboxyl, amine, thiol, ester, succinimidyl ester, azide, alkyne, cyclooctyne, or phosphine groups.

In some aspects, Pdots can be used that contain a polymer functionalized on the terminal monomeric unit, for example with a carboxyl, amine, thiol, ester, succinimidyl ester, azide, alkyne, cyclooctyne, phosphine, or similar functional group. Examples of polymers that can be used include, without limitation, poly(meth)acrylate polymers, polyacrylamide polymers, polyisobutylene, polydiene, polyphenylene, polyethylene, poly(ethylene glycol), polylactide, polystyrene, polysiloxane, polyvinyl pyridine), poly(vinylpyrrolidone), polyurethane, a block copolymer thereof, a random or alternating copolymer thereof, and the like.

In some aspects, Pdots can be used that contain a copolymer having one or more functionalized monomeric units, for example an amphiphilic polymer, including but not limited to: poly((meth)acrylic acid)-based copolymers such as: poly(acrylic acid-b-acrylamide), poly(acrylic acid-b-methyl methacrylate), poly(acrylic acid-b-N-isopropylacrylamide), poly(n-butylacrylate-b-acrylic acid), poly(sodium acrylate-b-methyl methacrylate), poly(methacrylic acid-b-neopentyl methacrylate), poly(methyl methacrylate-b-acrylic acid), poly(methyl methacrylate-b-methacrylic acid), poly(methyl methacrylate-b-N,N-dimethyl acrylamide), poly(methyl methacrylate-b-sodium acrylate), poly(methyl methacrylate-b-sodium methacrylate), poly(neopentyl methacrylate-b-methacrylic acid), poly(t-butyl methacrylate-b-ethylene oxide), poly(2-acrylamido-2-methylpropanesulfonic acid-b-acrylic acid); polydiene-based copolymers such as: poly(butadiene(1,2 addition)-b-ethylene oxide), poly(butadiene(1,2 addition)-b-methylacrylic acid, poly(butadiene(1,4 addition)-b-acrylic acid), poly(butadiene (1,4 addition)-b-ethylene oxide, poly(butadiene(1,4 addition)-b-sodium acrylate), poly(butadiene(1,4 addition)-b-N-methyl pyridinium iodide), poly(isoprene-b-ethylene oxide), poly(isoprene-b-ethylene oxide), and poly(isoprene-b-N-methyl 2-vinyl pyridinium iodide); poly(ethylene oxide)-based copolymers such as: poly(ethylene oxide-b-acrylic acid), poly(ethylene oxide-b-acrylamide), poly(ethylene oxide-b-butylene oxide), poly(ethylene oxide-b-c-caprolactone), poly(ethylene oxide-b-lactide), poly(ethylene oxide-b-lactide), poly(ethylene oxide-b-methacrylic acid), poly (ethylene oxide-b-methyl acrylate), poly(ethylene oxide-b-N-isopropylacrylamide), poly(ethylene oxide-b-methyl methacrylate), poly(ethylene oxide-b-nitrobenzyl methacrylate), poly(ethylene oxide-b-N,N-dimethylaminoethylmethacrylate), poly(ethylene oxide-b-propylene oxide), poly(ethylene oxide-b-t-butyl acrylate), poly(ethylene oxide-h-t-butyl methacrylate), poly(ethylene oxide-b-tetrahydrofurfuryl methacrylate), poly(ethylene oxide-b-2-ethyl oxazoline), poly(ethylene oxide-b-2-hydroxyethyl methacrylate), poly(ethylene oxide-b-2-methyl oxazoline); polyisobutylene-based copolymers such as poly(isobutylene-b-acrylic acid), poly(isobutylene-b-ethylene oxide), poly(isobutylene-b-methacrylic acid); polystyrene based copolymers such as poly(styrene-b-acrylamide), poly(styrene-b-acrylic acid), poly(styrene-h-cesium acrylate), poly (styrene-b-ethylene oxide), poly(styrene-b-ethylene oxide) acid cleavable at the block junction, poly(styrene-b-methacrylic acid), poly(4-styrenesulfonic acid-b-ethylene oxide), poly(styrenesulfonic acid-b-methylbutylene), poly(styrene-b-N,N-dimethylacrylamide), poly(styrene-b-N-isopropyl acrylamide), poly(styrene-b-N-methyl 2-vinyl pyridinium iodide), poly(styrene-b-N-methyl-4-vinyl pyridinium iodide), poly(styrene-b-propylactylic acid), poly(styrene-b-sodium acrylate) poly(styrene-b-sodium methacrylate), polyp-chloromethyl styrene-b-acrylamide), poly(styrene-co-p-chloromethyl styrene-b-acrylamide), poly(styrene-co-p-chloromethyl styrene-b-acrylic acid), poly(styrene-b-methylbutylene-co-isoprene sulfonate); polysiloxane-based copolymers such as poly(dimethylsiloxane-b-acrylic acid), poly(dimethylsiloxane-b-ethylene oxide), poly(dimethylsiloxane-b-methacrylic acid); poly(ferrocenyldimethylsilane) based copolymers such as poly(ferrocenyldimethylsilane-b-ethylene oxide); poly(2-vinyl naphthalene)-based copolymers such as poly(2-vinyl naphthalene-b-acrylic acid), poly(vinyl pyridine and N-methyl vinyl pyridinium iodide)-based copolymers such as poly(2-vinyl pyridine-b-ethylene oxide), poly(2-vinyl pyridine-h-methyl acrylic acid), poly(N-methyl 2-vinyl pyridinium iodide-b-ethylene oxide), poly(N-methyl 4-vinyl pyridinium iodide-b-methyl methacrylate), poly(4-vinyl pyridine-b-ethylene oxide) PEO end functional OH; and polyvinyl pyrrolidone)-based copolymers such as poly(vinyl pyrrolidone-b-D/L-lactide); and the like.

In some aspects of the present disclosure, Pdots used for detection can comprise the polymer, CN-PPV, which is a bright, compact, and orange-emitting semiconducting polymer dot also known as, poly[2-methoxy-5-(2-ethylhexyloxy)-1,4-(1-cyanovinylene-1,4-phenylene)]. CN-PPV has superior fluorescence properties, such as a large absorption cross-section, high quantum yield, and a fast emission rate.

In some aspects, the Pdot used for detecting proteins and peptides can comprises a polymer that consists essentially of CN-PPV. In some aspects, the nanoparticle includes CN-PPV and at least one other material. For example, the CN-PPV can be mixed with a copolymer or other material that provides an additional functionality.

In some aspects, the polymer dots used for the detection of proteins and peptides can include a semiconducting copolymer having at least two different chromophoric units. For example, a conjugated copolymer can contain both fluorene and benzothiazole chromophoric units present at a given ratio. Typical chromophoric units used to synthesize semiconducting copolymers include, but are not limited to fluorene unit, phenylene vinylene unit, phenylene unit, phenylene ethynylene unit, benzothiazole unit, thiophene unit, carbazole fluorene unit, boron-dipyrromethene unit, and derivatives thereof. The different chromophoric units can be segregated, as in a block copolymer, or intermingled. As used herein, a chromophoric copolymer is represented by writing the identity of the major chromophoric species. For example, PFBT is a chromophoric polymer containing fluorene and benzothiazole units at a certain ratio. In some cases, a dash is used to indicate the percentage of the minor chromophoric species and then the identity of the minor chromophoric species. For example, PF-0.1 BT is a chromophoric copolymer containing 90% PF and 10% BT.

In certain aspects, the polymer dots can include a blend of semiconducting polymers. The blends can include any combination of homopolymers, copolymers, and oligomers. Polymer blends used to form polymer dots may be selected in order to tune the properties of the resulting polymer dots, for example, to achieve a desired excitation or emission spectra for the polymer dot.

For some assays, semiconducting Pdots offer improved detection sensitivity in part because they exhibit higher quantum yields than other fluorescent reporters. In some aspects, the quantum yield of the Pdot used is more than 20%, more than 30%, more than 40%, more than 50%, more than 60%, more than 70%, more than 80%, or more than 90%.

For some assays, semiconducting Pdots offer improved detection sensitivity in part because they exhibit faster emission rates than other fluorescent reporters. In certain aspects, the emission rate of the Pdot used is between about 0.1 nanoseconds and about 50 nanoseconds.

In some aspects, the chromophoric polymer dot used comprises polymers bearing units of small organic dye molecules, metal complexes, photochotochromic dye, and any combinations thereof, for example, optically inactive polymers such as polystyrene covalently linked or grafted with small organic dye, metal complexes, photochromic dyes and any combination thereof. These dyes or metal complexes may have protein sensing capability.

In some aspects, methods, systems, compositions and kits are provided for the use of Pdots comprising semiconducting polymers covalently linked with small organic dye molecules, metal complexes, photochromic dyes, and any combinations thereof as emissive units. Such emissive units can tune the emission color, increase the quantum yield, and improve the photostability of the chromophoric polymer dot.

In some aspects, the small organic dyes, or metal complexes can have sensing functions, and therefore add additional functionalities to the chromophoric polymer dot, such as protein sensing capability.

In some aspects, the Pdot may comprise a semiconducting polymer physically mixed or chemically cross-linked with other chromophoric polymer such as optically inactive polymer covalently linked or grafted with small organic dye, metal complexes, photochromic dyes and any combination thereof, to have additional functionalities such as protein sensing.

In some aspects, the Pdot may comprise semiconducting polymers physically mixed or chemically cross-linked with other components such as fluorescent dyes, inorganic luminescent materials, magnetic materials, metal materials, and the like in order to tune emission color, improve quantum yield and/or photostability, and/or provide additional functionalities such as magnetic functions, plasmon resonance functions, and the like.

Sizes of the nanoparticles provided herein are defined in terms of a "critical dimension," which refers to the smallest dimension of the nanoparticle. Many nanoparticles are roughly spherical in shape, which results in the critical dimension being the radius or diameter of the spherical particle. While typical nanoparticles, such as nanospheres and nanocubes, are completely nanoscopic in size, not every dimension of a nanoparticle needs to be at the nanoscale. For example, a nano-cylinder may have a diameter on the nano-scale but a length on the micro-scale.

In some aspects, the critical dimension of the Pdot used is 30 nm or less. In some aspects, the critical dimension is 25 nm or less. In some aspects, the critical dimension is 20 nm or less. In some aspects, the critical dimension is 15 nm or less. In some aspects, the critical dimension is 10 nm or less. In some aspects, the critical dimension is 5 nm or less.

In some aspects, the Pdot used has a critical dimension greater than 1 nm and less than 1000 nm.

The possible shape of the nanoparticle is essentially unlimited. However, in certain aspects, the shape is selected from a sphere, a cylinder, an ellipsoid, a polyhedron, a prism, a rod, and a wire. The shape of the nanoparticle can contribute to the detection properties, as will be appreciated by those of skill in the art (e.g., nano-rods may have different optical properties than nano-spheres).

The nano-scale size of the nanoparticle is essential in order to bypass issues presented by large particle sizes. For example, when attaching nanoparticles to a target molecule (e.g., a protein) for photoluminescence imaging, relatively large particles have more surface area available for non-specific binding to molecules other than the target, or adsorption to a surface.

The provided nanoparticles are optimized for use as photo-luminescent reporters that can be attached to a target molecule as part of an analysis method, system or kit. The nanoparticles should be easily detectable using photoluminescence and should have specificity for their target molecules.

The optical properties, such as absorption wavelength, for a given Pdot can be tuned by modifying its composition and geometry. Semiconducting polymers have been developed with absorption wavelengths ranging from UV to infrared, including the entire visible spectrum. In some aspects, Pdots having a peak absorption wavelength between about 200 nm and about 300 nm, about 250 nm and about 350 nm, about 300 nm and about 400 nm, about 350 nm and about 450 nm, between about 400 nm and about 500 nm, about 450 nm and about 550 nm, about 500 nm and about 600 nm, about 550 nm and about 650 nm, about 600 nm and about 700 nm, about 650 nm and about 750 nm, about 700 nm and about 800 nm, about 750 nm and about 850 nm, about 800 nm and about 900 nm, about 850 nm and about 950 nm, or about 900 nm and about 1000 nm are used.

Semiconducting polymers have been developed with emission wavelengths ranging from UV to infrared, including the entire visible spectrum. In some aspects, Pdots having a peak emission wavelength between about 200 nm and about 300 nm, about 250 nm and about 350 nm, about 300 nm and about 400 nm, about 350 nm and about 450 nm, about 400 nm and about 500 nm, about 450 nm and about 550 nm, about 500 nm and about 600 nm, about 550 nm and about 650 nm, about 600 nm and about 700 nm, about 650 nm and about 750 nm, about 700 nm and about 800 nm, about 750 nm and about 850 nm, about 800 nm and about 900 nm, about 850 nm and about 950 nm, about 900 nm and about 1000 nm, about 950 nm and about 1050 nm, about 1000 nm and about 1100 nm, about 1150 nm and about 1250 nm, or about 1200 nm and about 1300 nm are used.

In some aspects, the methods, systems, compositions and kits provided will make use of Pdots with narrow-band emissions. Narrow-band emissions are advantageous for certain applications, including but not limited to multiplexing applications. The emission wavelength of the polymer dots can vary from ultraviolet to near infrared region. The full width at half maximum (FWHM) of the emission band is less than 70 nm. In some embodiments, the FWHM is less than about 65 nm. In some embodiments, the FWHM is less than about 60 nm. In some embodiments, the FWHM is less than about 55 nm. In some embodiments, the FWHM is less than about 50 nm. In some embodiments, the FWHM is less than about 45 nm. In some embodiments, the FWHM is less than about 40 nm. In some embodiments, the FWHM is less than about 35 nm. In some embodiments, the FWHM is less than about 30 nm. In some embodiments, the FWHM is less than about 25 nm. In some embodiments, the FWHM is less than about 20 nm. In some embodiments, the FWHM is less than about 10 nm. In some embodiments, the FWHM of the polymer dots described herein can range between about 5 nm to about 70 nm, from about 10 nm to about 60 nm, from about 20 nm to about 50 nm, or from about 30 nm to about 45 nm.

In some aspects, the narrow-band emissive polymers for making Pdots include boron-dipyrromethene (4,4-difluoro-4-bora-3a,4a-diaza-s-indacene, BODIPY) and or their derivatives, and/or other boron-containing monomers and their derivatives, as narrow-band monomers. BODIPY and other boron containing monomers and their derivatives include but are not limited to their alkyl derivatives, aryl derivatives, alkyne derivatives, aromatic derivatives, alkoxide derivatives, aza derivatives, BODIPY extended systems and other BODIPY derivatives. The narrow-band emissive polymers can also include any other monomers. The BODIPY based-monomers can be energy acceptors and other monomers can be energy donors so that the final Pdots can exhibit narrow-band emissions. The narrowband emissive chromophoric polymers in good solvents may exhibit broad emissions or narrow emissions. A comprehensive description of Pdots with narrow-band emissions, including BODIPY and other boron containing monomers and their derivatives, is described in WO2013/101902, which is herein incorporated by reference in its entirety.

As will be appreciated by one of ordinary skill in the art, the various chemical terms defined herein can be used for describing chemical structures of the polymers and monomers of the present disclosure. For example, a variety of the monomer derivatives (e.g., BODIPY derivatives) can include a variety of the chemical substituents and groups described herein. For example, in some embodiments, derivatives of the various monomers can be substituted with hydrogen, deuterium, alkyl, aralkyl, aryl, alkoxy-aryl, N-dialkyl-4-phenyl, N-diphenyl-4-phenyl, N-dialkoxyphenyl-4-phenyl, amino, sulfide, aldehyde, ester, ether, acid, and/or hydroxyl. The present invention can include polymer dots, e.g., narrow-band emissive chromophoric polymer dots. As described further herein, the present invention includes a wide variety of polymer dots that exhibit narrow band emission properties (e.g., a FWHM less than 70 nm). As described further herein, the variety of polymer dots of the present invention can include polymers that have a narrow band emissive unit (e.g., a narrow band monomer and/or a narrow band unit). For example, the present invention can include a homopolymer or heteropolymer including a narrow band monomer, such as BODIPY and/or BODIPY derivative monomer, a squaraine and/or squaraine derivative, a metal complex and/or metal complex derivative monomer, a porphyrin and/or porphyrin derivative monomer, a phthalocyanine and/or phthalocynanine derivative monomer, a lanthanide complex and/or lanthanide complex derivative monomer, a perylene and/or perylene derivative monomer, a cyanine and/or cyanine derivative monomer, a rhodamine and/or rhodamine derivative monomer, a coumarin and/or coumarin derivative monomer, and/or a xanthene and/or xanthene derivative monomer. A narrow band unit can be, e.g., a narrow band monomer or a fluorescent nanoparticle embedded in or attached to the polymer dot. The fluorescent nanoparticle can be, e.g., a quantum dot. A narrow band unit can also include a polymer or fluorescent dye molecule that gives a narrow emission in a polymer dot of the present invention.

A variety of other BODIPY derivatives can be used for the present invention. BODIPY and BODIPY derivatives can be polymerized to form polymers (e.g., homopolymers or heteropolymers) and/or can be attached (e.g., covalently attached) to a polymer backbone, sidechain and/or terminus. In some embodiments, the chromophoric polymer dots of the present invention can include a polymer that includes a narrow-band monomer having the structure of Formula (I):

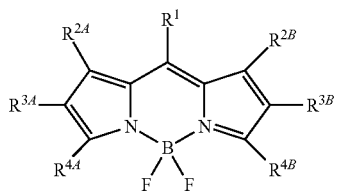

(I)

wherein each of $R^1$, $R^{2A}$, $R^{2B}$, $R^{3A}$, $R^{3B}$, $R^{4A}$ and $R^{4B}$ is independently selected from the group consisting of, but not limited to, hydrogen (H), deuterium (D), halogen, direct or branched alkyl, heteroalkyl, heterocycloalkyl, heterocycloalkylene, alkoxy, aryl, hydroxyl, cyano, nitro, ether and its derivatives, ester and its derivatives, alkyl ketone, alkylester, arylester, alkynyl, alkyl amine, fluoroalkyl, fluoroaryl, and polyalkalene (e.g., mehtoxyethoxyethoxy, ethoxyethoxy, and $(OCH_2CH_2)_nOH$, n=1-50), phenyl, alkyl-(alkoxy-, aryl-, fluoroalkyl-, fluoroaryl-)substituted phenyl, pyridyl, alkyl-(alkoxy-, aryl-, fluoroalkyl-, fluoroaryl-)substituted pyridyl, bipyridyl, alkyl-(alkoxy-, aryl-, fluoroalkyl-, fluoroaryl-)substituted bipyridyl tripyridyl, alkyl-(alkoxy-, aryl-, fluoroalkyl-, fluoroaryl-)substituted tripyridyl, furyl, alkyl-(alkoxy-, aryl-, fluoroalkyl-, fluoroaryl-)substituted furyl, thienyl, alkyl-(alkoxy-, aryl-, fluoroalkyl-, fluoroaryl-)substituted thienyl, pyrrolyl, alkyl-(alkoxy-, aryl-, fluoroalkyl-, fluoroaryl-)substituted pyrrolyl, pyrazolyl, alkyl-(alkoxy-, aryl-, fluoroalkyl-, fluoroaryl-)substituted pyrazolyl, oxazolyl, alkyl-(alkoxy-, aryl-, fluoroalkyl-, fluoroaryl-)substituted oxazolyl, thiazolyl, alkyl-(alkoxy-, aryl-, fluoroalkyl-, fluoroaryl-)substituted thiazolyl, imidazolyl, alkyl-(alkoxy-, aryl-, fluoroalkyl-, fluoroaryl-) substituted imidazolyl, pyrazinyl, alkyl-(alkoxy-, aryl-, fluoroalkyl-, fluoroaryl-)substituted pyrazinyl, benzooxadizolyl, alkyl-(alkoxy-, aryl-, fluoroalkyl-, fluoroaryl-)substituted benzooxadizolyl, benzothiadizolyl, alkyl-(alkoxy-, aryl-, fluoroalkyl-, fluoroaryl-)substituted benzothiadizolyl, fluorenyl, alkyl-(alkoxy-, aryl-, fluoroalkyl-, fluoroaryl-)substituted fluorenyl, triphenylaminyl-substituted fluorenyl, diphenylaminyl-substituted fluorenyl, alkyl-substituted carbazolyl, alkyl-substituted triphenylaminyl and alkyl-substituted thiophenyl. As exemplary embodiments, alkyl substituted phenyl can include 2-alkylphenyl, 3-alkylphenyl, 4-alkylphenyl, 2,4-dialkylphenyl, 3,5-dialkylphenyl, 3,4-dialkylphenyl; alkyl-substituted fluorenyl can include 9,9-dialkyl-substituted fluorenyl, 7-alkyl-9,9-dialkyl-substituted fluorenyl, 6-alkyl-9,9-dialkyl-substituted fluorenyl, 7-triphenylaminyl-9,9-dialkyl-substituted fluorenyl and 7-diphenylaminyl-9,9-dialkyl-substituted fluorenyl; alkyl-substituted carbazolyl can include N-alkyl-substituted carbazolyl, 6-alkyl-substituted carbazolyl and 7-alkyl-substituted carbazolyl; alkyl-substituted triphenylaminyl can include 4'-alkyl-substituted triphenylaminyl, 3'-alkyl-substituted triphenylaminyl, 3',4'-dialkyl-substituted triphenylaminyl and 4',4"-alkyl-substituted triphenylaminyl; alkyl-substituted thiophenyl can include 2-alkylthiophenyl, 3-alkylthiophenyl, and 4-alkylthiophenyl, N-dialkyl-4-phenyl, N-diphenyl-4-phenyl, and N-dialkoxyphenyl-4-phenyl. The narrow-band monomer can be integrated into a backbone of the polymer (e.g., polymerized in the polymer) and/or covalently attached to the backbone, a terminus, or a sidechain of the polymer, through at least one attachment to $R^1$, $R^{2A}$, $R^{2B}$, $R^{3A}$, $R^{3B}$, $R^{4A}$, $R^{4B}$, or a combination thereof.

In some embodiments, the chromophoric polymer dots of the present invention can include a polymer that includes a narrow-band monomer having the structure of Formula (II):

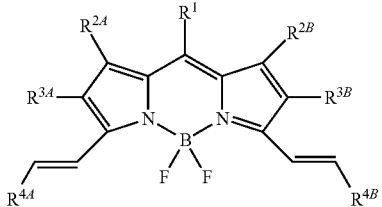

(II)

wherein each of $R^1$, $R^{2A}$, $R^{2B}$, $R^{3A}$, $R^{3B}$, $R^{4A}$ and $R^{4B}$ is independently selected from the group consisting of, but not limited to, hydrogen (H), deuterium (D), halogen, direct or branched alkyl, heteroalkyl, heterocycloalkyl, heterocycloalkylene, alkoxy, aryl, hydroxyl, cyano, nitro, ether and its derivatives, ester and its derivatives, alkyl ketone, alkylester, arylester, alkynyl, alkyl amine, fluoroalkyl, fluoroaryl, and polyalkalene (e.g, mehtoxyethoxyethoxy, ethoxyethoxy, and $(OCH_2CH_2)_nOH$, n=1-50), phenyl, alkyl-(alkoxy-, aryl-, fluoroalkyl-, fluoroaryl-)substituted phenyl, pyridyl, alkyl-(alkoxy-, aryl-, fluoroalkyl-, fluoroaryl-)substituted pyridyl, bipyridyl, alkyl-(alkoxy-, aryl-, fluoroalkyl-, fluoroaryl-)substituted bipyridyl tripyridyl, alkyl-(alkoxy-, aryl-, fluoroalkyl-, fluoroaryl-)substituted tripyridyl, furyl, alkyl-(alkoxy-, aryl-, fluoroalkyl-, fluoroaryl-)substituted furyl, thienyl, alkyl-(alkoxy-, aryl-, fluoroalkyl-, fluoroaryl-)substituted thienyl, pyrrolyl, alkyl-(alkoxy-, aryl-, fluoroalkyl-, fluoroaryl-)substituted pyrrolyl, pyrazolyl, alkyl-(alkoxy-, aryl-, fluoroalkyl-, fluoroaryl-)substituted pyrazolyl, oxazolyl, alkyl-(alkoxy-, aryl-, fluoroalkyl-, fluoroaryl-)substituted oxazolyl, thiazolyl, alkyl-(alkoxy-, aryl-, fluoroalkyl-, fluoroaryl-)substituted thiazolyl, imidazolyl, alkyl-(alkoxy-, aryl-, fluoroalkyl-, fluoroaryl-) substituted imidazolyl, pyrazinyl, alkyl-(alkoxy-, aryl-, fluoroalkyl-, fluoroaryl-)substituted pyrazinyl, benzooxadizolyl, alkyl-(alkoxy-, aryl-, fluoroalkyl-, fluoroaryl-)substituted benzooxadizolyl, benzothiadizolyl, alkyl-(alkoxy-, aryl-, fluoroalkyl-, fluoroaryl-)substituted benzothiadizolyl, fluorenyl, alkyl-(alkoxy-, aryl-, fluoroalkyl-, fluoroaryl-)substituted fluorenyl, triphenylaminyl-substituted fluorenyl, diphenylaminyl-substituted fluorenyl, alkyl-substituted carbazolyl, alkyl-substituted triphenylaminyl and alkyl-substituted thiophenyl. As exemplary embodiments, alkyl substituted phenyl can include 2-alkylphenyl, 3-alkylphenyl, 4-alkylphenyl, 2,4-dialkylphenyl, 3,5-dialkylphenyl, 3,4-dialkylphenyl; alkyl-substituted fluorenyl can include 9,9-dialkyl-substituted fluorenyl, 7-alkyl-9,9-dialkyl-substituted fluorenyl, 6-alkyl-9,9-dialkyl-substituted fluorenyl, 7-triphenylaminyl-9,9-dialkyl-substituted fluorenyl and 7-diphenylaminyl-9,9-dialkyl-substituted fluorenyl; alkyl-substituted carbazolyl can include N-alkyl-substituted carbazolyl, 6-alkyl-substituted carbazolyl and 7-alkyl-substituted carbazolyl; alkyl-substituted triphenylaminyl can include 4'-alkyl-substituted triphenylaminyl, 3'-alkyl-substituted triphenylaminyl, 3',4'-dialkyl-substituted triphenylaminyl and 4',4"-alkyl-substituted triphenylaminyl; alkyl-substituted thiophenyl can include 2-alkylthiophenyl, 3-alkylthiophenyl, and 4-alkylthiophenyl, N-dialkyl-4-phenyl, N-diphenyl-4-phenyl, and N-dialkoxyphenyl-4-phenyl. The narrow-band monomer can be integrated into a backbone of the polymer (e.g., polymerized in the polymer) and/or covalently attached to the backbone, a terminus, or a sidechain of the polymer through at least one attachment to $R^1$, $R^{2A}$, $R^{2B}$, $R^{3A}$, $R^{3B}$, $R^{4A}$, $R^{4B}$, or a combination thereof. The monomer can, for example, integrate with the backbone of the polymer by attachment to the $R^{3A}$ and $R^{3B}$ groups.

In some embodiments, the chromophoric polymer dots of the present invention can include a polymer that includes a narrow-band monomer having the structure of Formula (III):

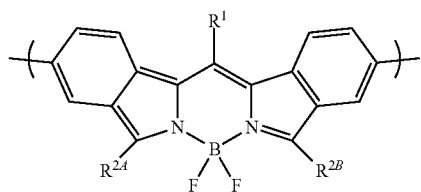

(III)

wherein each of $R^1$, $R^{2A}$ and $R^{2B}$ is independently selected from the group consisting of, but not limited to, hydrogen (H), deuterium (D), halogen, direct or branched alkyl, heteroalkyl, heterocycloalkyl, heterocycloalkylene, alkoxy, aryl, hydroxyl, cyano, nitro, ether and its derivatives, ester and its derivatives, alkyl ketone, alkylester, arylester, alkynyl, alkyl amine, fluoroalkyl, fluoroaryl, and polyalkalene (e.g, mehtoxyethoxyethoxy, ethoxyethoxy, and $(OCH_2CH_2)_nOH$, n=1-50), phenyl, alkyl-(alkoxy-, aryl-, fluoroalkyl-, fluoroaryl-)substituted phenyl, pyridyl, alkyl-(alkoxy-, aryl-, fluoroalkyl-, fluoroaryl-)substituted pyridyl, bipyridyl, alkyl-(alkoxy-, aryl-, fluoroalkyl-, fluoroaryl-)substituted bipyridyl tripyridyl, alkyl-(alkoxy-, aryl-, fluoroalkyl-, fluoroaryl-)substituted tripyridyl, furyl, alkyl-(alkoxy-, aryl-, fluoroalkyl-, fluoroaryl-)substituted furyl, thienyl, alkyl-(alkoxy-, aryl-, fluoroalkyl-, fluoroaryl-)substituted thienyl, pyrrolyl, alkyl-(alkoxy-, aryl-, fluoroalkyl-, fluoroaryl-)substituted pyrrolyl, pyrazolyl, alkyl-(alkoxy-, aryl-, fluoroalkyl-, fluoroaryl-)substituted pyrazolyl, oxazolyl, alkyl-(alkoxy-, aryl-, fluoroalkyl-, fluoroaryl-)substituted oxazolyl, thiazolyl, alkyl-(alkoxy-, aryl-, fluoroalkyl-, fluoroaryl-)substituted thiazolyl, imidazolyl, alkyl-(alkoxy-, aryl-, fluoroalkyl-, fluoroaryl-) substituted imidazolyl, pyrazinyl, alkyl-(alkoxy-, aryl-, fluoroalkyl-, fluoroaryl-) substituted pyrazinyl, benzooxadizolyl, alkyl-(alkoxy-, aryl-, fluoroalkyl-, fluoroaryl-)substituted benzooxadizolyl, benzothiadizolyl, alkyl-(alkoxy-, aryl-, fluoroalkyl-, fluoroaryl-)substituted benzothiadizolyl, fluorenyl, alkyl-(alkoxy-, aryl-, fluoroalkyl-, fluoroaryl-)substituted fluorenyl, triphenylaminyl-substituted fluorenyl, diphenylaminyl-substituted fluorenyl, alkyl-substituted carbazolyl, alkyl-substituted triphenylaminyl and alkyl-substituted thiophenyl. As exemplary embodiments, alkyl substituted phenyl can include 2-alkylphenyl, 3-alkylphenyl, 4-alkylphenyl, 2,4-dialkylphenyl, 3,5-dialkylphenyl, 3,4-dialkylphenyl; alkyl-substituted fluorenyl can include 9,9-dialkyl-substituted fluorenyl, 7-alkyl-9,9-dialkyl-substituted fluorenyl, 6-alkyl-9,9-dialkyl-substituted fluorenyl, 7-triphenylaminyl-9,9-dialkyl-substituted fluorenyl and 7-diphenylaminyl-9,9-dialkyl-substituted fluorenyl; alkyl-substituted carbazolyl can include N-alkyl-substituted carbazolyl, 6-alkyl-substituted carbazolyl and 7-alkyl-substituted carbazolyl; alkyl-substituted triphenylaminyl can include 4'-alkyl-substituted triphenylaminyl, 3'-alkyl-substituted triphenylaminyl, 3',4'-dialkyl-substituted triphenylaminyl and 4',4''-alkyl-substituted triphenylaminyl; alkyl-substituted thiophenyl can include 2-alkylthiophenyl, 3-alkylthiophenyl, and 4-alkylthiophenyl, N-dialkyl-4-phenyl, N-diphenyl-4-phenyl, and N-dialkoxyphenyl-4-phenyl. The narrow-band monomer can be integrated into a backbone of the polymer (e.g., polymerized in the polymer) and/or covalently attached to the backbone, a terminus, or a sidechain of the polymer through at least one attachment, e.g., to $R^1$, $R^{2A}$, $R^{2B}$, or a combination thereof. The parentheses indicate points of attachment of the monomer to the backbone of the polymer.

In some embodiments, the chromophoric polymer dots of the present invention can include a polymer that includes a narrow-band monomer having the structure of Formula (IV):

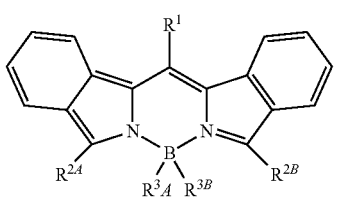

(IV)

wherein each of $R^1$, $R^{2A}$, $R^{2B}$, $R^{3A}$, and $R^{3B}$ is independently selected from the group consisting of, but not limited to, hydrogen (H), deuterium (D), halogen, direct or branched alkyl, heteroalkyl, heterocycloalkyl, heterocycloalkylene, alkoxy, aryl, hydroxyl, cyano, nitro, ether and its derivatives, ester and its derivatives, alkyl ketone, alkylester, arylester, alkynyl, alkyl amine, fluoroalkyl, fluoroaryl, and polyalkalene (e.g. mehtoxyethoxyethoxy, ethoxyethoxy, and $(OCH_2CH_2)_nOH$, n=1-50), phenyl, alkyl-(alkoxy-, aryl-, fluoroalkyl-, fluoroaryl-)substituted phenyl, pyridyl, alkyl-(alkoxy-, aryl-, fluoroalkyl-, fluoroaryl-)substituted pyridyl, bipyridyl, alkyl-(alkoxy-, aryl-, fluoroalkyl-, fluoroaryl-)substituted bipyridyl tripyridyl, alkyl-(alkoxy-, aryl-, fluoroalkyl-, fluoroaryl-)substituted tripyridyl, furyl, alkyl-(alkoxy-, aryl-, fluoroalkyl-, fluoroaryl-)substituted furyl, thienyl, alkyl-(alkoxy-, aryl-, fluoroalkyl-, fluoroaryl-)substituted thienyl, pyrrolyl, alkyl-(alkoxy-, aryl-, fluoroalkyl-, fluoroaryl-)substituted pyrrolyl, pyrazolyl, alkyl-(alkoxy-, aryl-, fluoroalkyl-, fluoroaryl-)substituted pyrazolyl, oxazolyl, alkyl-(alkoxy-, aryl-, fluoroalkyl-, fluoroaryl-)substituted oxazolyl, thiazolyl, alkyl-(alkoxy-, aryl-, fluoroalkyl-, fluoroaryl-)substituted thiazolyl, imidazolyl, alkyl-(alkoxy-, aryl-, fluoroalkyl-, fluoroaryl-) substituted imidazolyl, pyrazinyl, alkyl-(alkoxy-, aryl-, fluoroalkyl-, fluoroaryl-) substituted pyrazinyl, benzooxadizolyl, alkyl-(alkoxy-, aryl-, fluoroalkyl-, fluoroaryl-)substituted benzooxadizolyl, benzothiadizolyl, alkyl-(alkoxy-, aryl-, fluoroalkyl-, fluoroaryl-)substituted benzothiadizolyl, fluorenyl, alkyl-(alkoxy-, aryl-, fluoroalkyl-, fluoroaryl-)substituted fluorenyl, triphenylaminyl-substituted fluorenyl, diphenylaminyl-substituted fluorenyl, alkyl-substituted carbazolyl, alkyl-substituted triphenylaminyl and alkyl-substituted thiophenyl. As exemplary embodiments, alkyl substituted phenyl can include 2-alkylphenyl, 3-alkylphenyl, 4-alkylphenyl, 2,4-dialkylphenyl, 3,5-dialkylphenyl, 3,4-dialkylphenyl; alkyl-substituted fluorenyl can include 9,9-dialkyl-substituted fluorenyl, 7-alkyl-9,9-dialkyl-substituted fluorenyl, 6-alkyl-9,9-dialkyl-substituted fluorenyl, 7-triphenylaminyl-9,9-dialkyl-substituted fluorenyl and 7-diphenylaminyl-9,9-dialkyl-substituted fluorenyl; alkyl-substituted carbazolyl can include N-alkyl-substituted carbazolyl, 6-alkyl-substituted carbazolyl and 7-alkyl-substituted carbazolyl; alkyl-substituted triphenylaminyl can include 4'-alkyl-substituted triphenylaminyl, 3'-alkyl-substituted triphenylaminyl, 3',4'-dialkyl-substituted triphenylaminyl and 4',4"-alkyl-substituted triphenylaminyl; alkyl-substituted thiophenyl can include 2-alkylthiophenyl, 3-alkylthiophenyl, and 4-alkylthiophenyl, N-dialkyl-4-phenyl, N-diphenyl-4-phenyl, and N-dialkoxyphenyl-4-phenyl. The narrow-band monomer can be integrated into a backbone of the polymer (e.g., polymerized in the polymer) and/or covalently attached to the backbone, a terminus, or a sidechain of the polymer through at least one attachment to $R^1$, $R^{2A}$, $R^{2B}$, $R^{3A}$, and $R^{3B}$ or a combination thereof.

In some embodiments, the chromophoric polymer dots of the present invention can include a polymer that includes a narrow-band monomer having the structure of Formula (V):

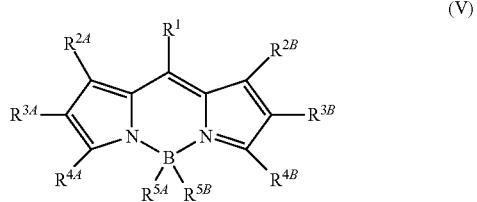

(V)

wherein each of $R^1$, $R^{2A}$, $R^{2B}$, $R^{3A}$, $R^{3B}$, $R^{4A}$, $R^{4B}$, $R^{5A}$, and $R^{5B}$ is independently selected from the group consisting of, but not limited to, hydrogen (H), deuterium (D), halogen, direct or branched alkyl, heteroalkyl, heterocycloalkyl, heterocycloalkylene, alkoxy, aryl, hydroxyl, cyano, nitro, ether and its derivatives, ester and its derivatives, alkyl ketone, alkylester, arylester, alkynyl, alkyl amine, fluoroalkyl, fluoroaryl, and polyalkalene (e.g, mehtoxyethoxyethoxy, ethoxyethoxy, and $(OCH_2CH_2)_nOH$, n=1-50), phenyl, alkyl-(alkoxy-, aryl-, fluoroalkyl-, fluoroaryl-) substituted phenyl, pyridyl, alkyl-(alkoxy-, aryl-, fluoroalkyl-, fluoroaryl-)substituted pyridyl, bipyridyl, alkyl-(alkoxy-, aryl-, fluoroalkyl-, fluoroaryl-)substituted bipyridyl tripyridyl, alkyl-(alkoxy-, aryl-, fluoroalkyl-, fluoroaryl-)substituted tripyridyl, furyl, alkyl-(alkoxy-, aryl-, fluoroalkyl-, fluoroaryl-)substituted furyl, thienyl, alkyl-(alkoxy-, aryl-, fluoroalkyl-, fluoroaryl-) substituted thienyl, pyrrolyl, alkyl-(alkoxy-, aryl-, fluoroalkyl-, fluoroaryl-)substituted pyrrolyl, pyrazolyl, alkyl-(alkoxy-, aryl-, fluoroalkyl-, fluoroaryl-) substituted pyrazolyl, oxazolyl, alkyl-(alkoxy-, aryl-, fluoroalkyl-, fluoroaryl-)substituted oxazolyl, thiazolyl, alkyl-(alkoxy-, aryl-, fluoroalkyl-, fluoroaryl-)substituted thiazolyl, imidazolyl, alkyl-(alkoxy-, aryl-, fluoroalkyl-, fluoroaryl-)substituted imidazolyl, pyrazinyl, alkyl-(alkoxy-, aryl-, fluoroalkyl-, fluoroaryl-) substituted pyrazinyl, benzooxadizolyl, alkyl-(alkoxy-, aryl-, fluoroalkyl-, fluoroaryl-) substituted benzooxadizolyl, benzothiadizolyl, alkyl-(alkoxy-, aryl-, fluoroalkyl-, fluoroaryl-) substituted benzothiadizolyl, fluorenyl, alkyl-(alkoxy-, aryl-, fluoroalkyl-, fluoroaryl-) substituted fluorenyl, triphenylaminyl-substituted fluorenyl, diphenylaminyl-substituted fluorenyl, alkyl-substituted carbazolyl, alkyl-substituted triphenylaminyl and alkyl-substituted thiophenyl. As exemplary embodiments, alkyl substituted phenyl can include 2-alkylphenyl, 3-alkylphenyl, 4-alkylphenyl, 2,4-dialkylphenyl, 3,5-dialkylphenyl, 3,4-dialkylphenyl; alkyl-substituted fluorenyl can include 9,9-dialkyl-substituted fluorenyl, 7-alkyl-9,9-dialkyl-substituted fluorenyl, 6-alkyl-9,9-dialkyl-substituted fluorenyl, 7-triphenylaminyl-9,9-dialkyl-substituted fluorenyl and 7-diphenylaminyl-9,9-dialkyl-substituted fluorenyl; alkyl-substituted carbazolyl can include N-alkyl-substituted carbazolyl, 6-alkyl-substituted carbazolyl and 7-alkyl-substituted carbazolyl; alkyl-substituted triphenylaminyl can include 4'-alkyl-substituted triphenylaminyl, 3'-alkyl-substituted triphenylaminyl, 3',4'-dialkyl-substituted triphenylaminyl and 4',4"-alkyl-substituted triphenylaminyl; alkyl-substituted thiophenyl can include 2-alkylthiophenyl, 3-alkylthiophenyl, and 4-alkylthiophenyl, N-dialkyl-4-phenyl, N-diphenyl-4-phenyl, and N-dialkoxyphenyl-4-phenyl. The narrow-band monomer can be integrated into a backbone of the polymer (e.g., copolymerized in the polymer) and/or covalently attached to the backbone, a terminus, or a sidechain of the polymer through at least one attachment to $R^1$, $R^{2A}$, $R^{2B}$, $R^{3A}$, $R^{3B}$, $R^{4A}$, $R^{4B}$, $R^{5A}$, $R^{5B}$, or a combination thereof. In certain embodiments, the narrow-band monomers can be integrated into the backbone by attachment to the $R^{5A}$ and $R^{5B}$ groups.

In some embodiments, the chromophoric polymer dots of the present invention can include a polymer that includes a narrow-band monomer having the structure of Formula (VI):

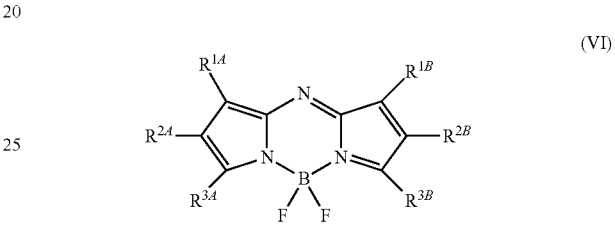

(VI)

wherein each of $R^{1A}$, $R^{1B}$, $R^{2A}$, $R^{2B}$, $R^{3A}$ and $R^{3B}$ is independently selected from the group consisting of, but not limited to, hydrogen (H), deuterium (D), halogen, direct or branched alkyl, heteroalkyl, heterocycloalkyl, heterocycloalkylene, alkoxy, aryl, hydroxyl, cyano, nitro, ether and its derivatives, ester and its derivatives, alkyl ketone, alkylester, arylester, alkynyl, alkyl amine, fluoroalkyl, fluoroaryl, and polyalkalene (e.g, mehtoxyethoxyethoxy, ethoxyethoxy, and $(OCH_2CH_2)_nOH$, n=1-50), phenyl, alkyl-(alkoxy-, aryl-, fluoroalkyl-, fluoroaryl-)substituted phenyl, pyridyl, alkyl-(alkoxy-, aryl-, fluoroalkyl-, fluoroaryl-)substituted pyridyl, bipyridyl, alkyl-(alkoxy-, aryl-, fluoroalkyl-, fluoroaryl-)substituted bipyridyl tripyridyl, alkyl-(alkoxy-, aryl-, fluoroalkyl-, fluoroaryl-)substituted tripyridyl, furyl, alkyl-(alkoxy-, aryl-, fluoroalkyl-, fluoroaryl-)substituted furyl, thienyl, alkyl-(alkoxy-, aryl-, fluoroalkyl-, fluoroaryl-)substituted thienyl, pyrrolyl, alkyl-(alkoxy-, aryl-, fluoroalkyl-, fluoroaryl-)substituted pyrrolyl, pyrazolyl, alkyl-(alkoxy-, aryl-, fluoroalkyl-, fluoroaryl-)substituted pyrazolyl, oxazolyl, alkyl-(alkoxy-, aryl-, fluoroalkyl-, fluoroaryl-)substituted oxazolyl, thiazolyl, alkyl-(alkoxy-, aryl-, fluoroalkyl-, fluoroaryl-)substituted thiazolyl, imidazolyl, alkyl-(alkoxy-, aryl-, fluoroalkyl-, fluoroaryl-) substituted imidazolyl, pyrazinyl, alkyl-(alkoxy-, aryl-, fluoroalkyl-, fluoroaryl-) substituted pyrazinyl, benzooxadizolyl, alkyl-(alkoxy-, aryl-, fluoroalkyl-, fluoroaryl-)substituted benzooxadizolyl, benzothiadizolyl, alkyl-(alkoxy-, aryl-, fluoroalkyl-, fluoroaryl-)substituted benzothiadizolyl, fluorenyl, alkyl-(alkoxy-, aryl-, fluoroalkyl-, fluoroaryl-)substituted fluorenyl, triphenylaminyl-substituted fluorenyl, diphenylaminyl-substituted fluorenyl, alkyl-substituted carbazolyl, alkyl-substituted triphenylaminyl and alkyl-substituted thiophenyl. As exemplary embodiments, alkyl substituted phenyl can include 2-alkylphenyl, 3-alkylphenyl, 4-alkylphenyl, 2,4-dialkylphenyl, 3,5-dialkylphenyl, 3,4-dialkylphenyl; alkyl-substituted fluorenyl can include 9,9-dialkyl-substituted fluorenyl, 7-alkyl-9,9-dialkyl-substituted fluorenyl, 6-alkyl-9,9-dialkyl-substituted fluorenyl, 7-triphenylaminyl-9,9-dialkyl-substituted fluorenyl and 7-diphenylaminyl-9,9-dialkyl-substituted fluorenyl; alkyl-substituted carbazolyl can include N-alkyl-substituted carbazolyl, 6-alkyl-substituted carbazolyl and 7-alkyl-substituted carbazolyl; alkyl-substituted triphenylaminyl can include 4'-alkyl-substituted triphenylaminyl, 3'-alkyl-substituted triphenylaminyl, 3',4'-dialkyl-substituted triphenylaminyl and 4',4"-alkyl-substituted triphenylaminyl; alkyl-substituted thiophenyl can include 2-alkylthiophenyl, 3-alkylthiophenyl, and 4-alkylthiophenyl, N-dialkyl-4-phenyl, N-diphenyl-4-phenyl, and N-dialkoxyphenyl-4-phenyl. The narrow-band monomer can be integrated into a backbone of the polymer (e.g., polymerized in the polymer) and/or covalently attached to the backbone, a terminus, or a sidechain of the polymer through at least one attachment to $R^{1A}$, $R^{1B}$, $R^{2A}$, $R^{2B}$, $R^{3A}$, $R^{3B}$, or a combination thereof.

In some embodiments, the chromophoric polymer dots of the present invention can include a polymer that includes a narrow-band monomer having the structure of Formula (VII):

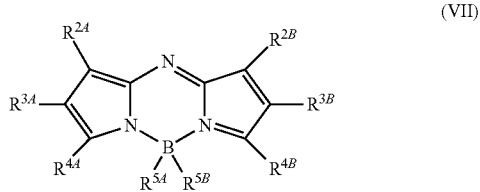

(VII)

wherein each of $R^{2A}$, $R^{2B}$, $R^{3A}$, $R^{3B}$, $R^{4A}$, $R^{4B}$, $R^{5A}$ and $R^{5B}$ is independently selected from the group consisting of, but not limited to, hydrogen (H), deuterium (D), halogen, direct or branched alkyl, heteroalkyl, heterocycloalkyl, heterocycloalkylene, alkoxy, aryl, hydroxyl, cyano, nitro, ether and its derivatives, ester and its derivatives, alkyl ketone, alkylester, arylester, alkynyl, alkyl amine, fluoroalkyl, fluoroaryl, and polyalkalene (e.g, mehtoxyethoxyethoxy, ethoxyethoxy, and $(OCH_2CH_2)_nOH$, n=1-50), phenyl, alkyl-(alkoxy-, aryl-, fluoroalkyl-, fluoroaryl-) substituted phenyl, pyridyl, alkyl-(alkoxy-, aryl-, fluoroalkyl-, fluoroaryl-)substituted pyridyl, bipyridyl, alkyl-(alkoxy-, aryl-, fluoroalkyl-, fluoroaryl-)substituted bipyridyl tripyridyl, alkyl-(alkoxy-, aryl-, fluoroalkyl-, fluoroaryl-)substituted tripyridyl, furyl, alkyl-(alkoxy-, aryl-, fluoroalkyl-, fluoroaryl-)substituted furyl, thienyl, alkyl-(alkoxy-, aryl-, fluoroalkyl-, fluoroaryl-) substituted thienyl, pyrrolyl, alkyl-(alkoxy-, aryl-, fluoroalkyl-, fluoroaryl-)substituted pyrrolyl, pyrazolyl, alkyl-(alkoxy-, aryl-, fluoroalkyl-, fluoroaryl-)substituted pyrazolyl, oxazolyl, alkyl-(alkoxy-, aryl-, fluoroalkyl-, fluoroaryl-)substituted oxazolyl, thiazolyl, alkyl-(alkoxy-, aryl-, fluoroalkyl-, fluoroaryl-)substituted thiazolyl, imidazolyl, alkyl-(alkoxy-, aryl-, fluoroalkyl-, fluoroaryl-)substituted imidazolyl, pyrazinyl, alkyl-(alkoxy-, aryl-, fluoroalkyl-, fluoroaryl-) substituted pyrazinyl, benzooxadizolyl, alkyl-(alkoxy-, aryl-, fluoroalkyl-, fluoroaryl-) substituted benzooxadizolyl, benzothiadizolyl, alkyl-(alkoxy-, aryl-, fluoroalkyl-, fluoroaryl-) substituted benzothiadizolyl, fluorenyl, alkyl-(alkoxy-, aryl-, fluoroalkyl-, fluoroaryl-) substituted fluorenyl, triphenylaminyl-substituted fluorenyl, diphenylaminyl-substituted fluorenyl, alkyl-substituted carbazolyl, alkyl-substituted triphenylaminyl and alkyl-substituted thiophenyl. As exemplary embodiments, alkyl substituted phenyl can include 2-alkylphenyl, 3-alkylphenyl, 4-alkylphenyl, 2,4-dialkylphenyl, 3,5-dialkylphenyl, 3,4-dialkylphenyl; alkyl-substituted fluorenyl can include 9,9-dialkyl-substituted fluorenyl, 7-alkyl-9,9-dialkyl-substituted fluorenyl, 6-alkyl-9,9-dialkyl-substituted fluorenyl, 7-triphenylaminyl-9,9-dialkyl-substituted fluorenyl and 7-diphenylaminyl-9,9-dialkyl-substituted fluorenyl; alkyl-substituted carbazolyl can include N-alkyl-substituted carbazolyl, 6-alkyl-substituted carbazolyl and 7-alkyl-substituted carbazolyl; alkyl-substituted triphenylaminyl can include 4'-alkyl-substituted triphenylaminyl, 3'-alkyl-substituted triphenylaminyl, 3',4'-dialkyl-substituted triphenylaminyl and 4',4"-alkyl-substituted triphenylaminyl; alkyl-substituted thiophenyl can include 2-alkylthiophenyl, 3-alkylthiophenyl, and 4-alkylthiophenyl, N-dialkyl-4-phenyl, N-diphenyl-4-phenyl, and N-dialkoxyphenyl-4-phenyl. The narrow-band monomer can be integrated into a backbone of the polymer (e.g., polymerized in the polymer) and/or covalently attached to the backbone, a terminus, or a sidechain of the polymer) through at least one attachment to $R^{2A}$, $R^{2B}$, $R^{3A}$, $R^{3B}$, $R^{4A}$, $R^{4B}$, $R^{5A}$, $R^{5B}$, or a combination thereof.

In some embodiments, the chromophoric polymer dots of the present invention can include a polymer that includes a narrow-band monomer having the structure of formula (VIII):

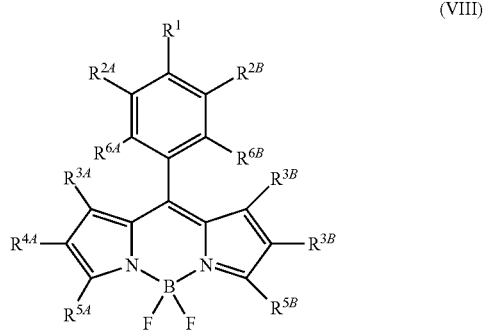

(VIII)

wherein each of $R^{1A}$, $R^{1B}$, $R^{2A}$, $R^{2B}$, $R^{3A}$, $R^{3B}$, $R^{4A}$ and $R^{4B}$, is independently selected from the group consisting of, but not limited to, hydrogen (H), deuterium (D), halogen, direct or branched alkyl, heteroalkyl, heterocycloalkyl, heterocycloalkylene, alkoxy, aryl, hydroxyl, cyano, nitro, ether and its derivatives, ester and its derivatives, alkyl ketone, alkylester, arylester, alkynyl, alkyl amine, fluoroalkyl, fluoroaryl, and polyalkalene (e.g, mehtoxyethoxyethoxy, ethoxyethoxy, and $(OCH_2CH_2)_nOH$, n=1-50), phenyl, alkyl-(alkoxy-, aryl-, fluoroalkyl-, fluoroaryl-) substituted phenyl, pyridyl, alkyl-(alkoxy-, aryl-, fluoroalkyl-, fluoroaryl-)substituted pyridyl, bipyridyl, alkyl-(alkoxy-, aryl-, fluoroalkyl-, fluoroaryl-)substituted bipyridyl tripyridyl, alkyl-(alkoxy-, aryl-, fluoroalkyl-, fluoroaryl-)substituted tripyridyl, furyl, alkyl-(alkoxy-, aryl-, fluoroalkyl-, fluoroaryl-)substituted furyl, thienyl, alkyl-(alkoxy-, aryl-, fluoroalkyl-, fluoroaryl-) substituted thienyl, pyrrolyl, alkyl-(alkoxy-, aryl-, fluoroalkyl-, fluoroaryl-)substituted pyrrolyl, pyrazolyl, alkyl-(alkoxy-, aryl-, fluoroalkyl-, fluoroaryl-)substituted pyrazolyl, oxazolyl, alkyl-(alkoxy-, aryl-, fluoroalkyl-, fluoroaryl-)substituted oxazolyl, thiazolyl, alkyl-(alkoxy-, aryl-, fluoroalkyl-, fluoroaryl-)substituted thiazolyl, imidazolyl, alkyl-(alkoxy-, aryl-, fluoroalkyl-, fluoroaryl-)substituted imidazolyl, pyrazinyl, alkyl-(alkoxy-, aryl-, fluoroalkyl-, fluoroaryl-) substituted pyrazinyl, benzooxadizolyl, alkyl-(alkoxy-, aryl-, fluoroalkyl-, fluoroaryl-) substituted benzooxadizolyl, benzothiadizolyl, alkyl-(alkoxy-, aryl-, fluoroalkyl-, fluoroaryl-) substituted benzothiadizolyl, fluorenyl, alkyl- (alkoxy-, aryl-, fluoroalkyl-, fluoroaryl-) substituted fluorenyl, triphenylaminyl-substituted fluorenyl, diphenylaminyl-substituted fluorenyl, alkyl-substituted carbazolyl, alkyl-substituted triphenylaminyl and alkyl-substituted thiophenyl. As exemplary embodiments, alkyl substituted phenyl can include 2-alkylphenyl, 3-alkylphenyl, 4-alkylphenyl, 2,4-dialkylphenyl, 3,5-dialkylphenyl, 3,4-dialkylphenyl; alkyl-substituted fluorenyl can include 9,9-dialkyl-substituted fluorenyl, 7-alkyl-9,9-dialkyl-substituted fluorenyl, 6-alkyl-9,9-dialkyl-substituted fluorenyl, 7-triphenylaminyl-9,9-dialkyl-substituted fluorenyl and 7-diphenylaminyl-9,9-dialkyl-substituted fluorenyl; alkyl-substituted carbazolyl can include N-alkyl-substituted carbazolyl, 6-alkyl-substituted carbazolyl and 7-alkyl-substituted carbazolyl; alkyl-substituted triphenylaminyl can include 4'-alkyl-substituted triphenylaminyl, 3'-alkyl-substituted triphenylaminyl, 3',4'-dialkyl-substituted triphenylaminyl and 4',4"-alkyl-substituted triphenylaminyl; alkyl-substituted thiophenyl can include 2-alkylthiophenyl, 3-alkylthiophenyl, and 4-alkylthiophenyl, N-dialkyl-4-phenyl, N-diphenyl-4-phenyl, and N-dialkoxyphenyl-4-phenyl and wherein each of $R^{5A}$, $R^{5B}$, $R^{6A}$ and $R^{6B}$ are independently selected from the group consisting of, but not limited to, hydrogen (H), deuterium (D), halogen, direct or branched alkyl, heteroalkyl, heterocycloalkyl, heterocycloalkylene, alkoxy, aryl, hydroxyl, cyano, nitro, ether and its derivatives, ester and its derivatives, alkyl ketone, alkylester, arylester, alkynyl, alkyl amine, fluoroalkyl, fluoroaryl, and polyalkalene (e.g, mehtoxyethoxyethoxy, ethoxyethoxy, and $(OCH_2CH_2)_nOH$, n=1-50), phenyl, alkyl-(alkoxy-, aryl-, fluoroalkyl-, fluoroaryl-)substituted phenyl, pyridyl, alkyl-(alkoxy-, aryl-, fluoroalkyl-, fluoroaryl-)substituted pyridyl, bipyridyl, alkyl-(alkoxy-, aryl-, fluoroalkyl-, fluoroaryl-)substituted bipyridyl tripyridyl, alkyl-(alkoxy-, aryl-, fluoroalkyl-, fluoroaryl-) substituted tripyridyl, furyl, alkyl-(alkoxy-, aryl-, fluoroalkyl-, fluoroaryl-)substituted furyl, thienyl, alkyl-(alkoxy-, aryl-, fluoroalkyl-, fluoroaryl-)substituted thienyl, pyrrolyl, alkyl-(alkoxy-, aryl-, fluoroalkyl-, fluoroaryl-)substituted pyrrolyl, pyrazolyl, alkyl-(alkoxy-, aryl-, fluoroalkyl-, fluoroaryl-)substituted pyrazolyl, oxazolyl, alkyl-(alkoxy-, aryl-, fluoroalkyl-, fluoroaryl-)substituted oxazolyl, thiazolyl, alkyl-(alkoxy-, aryl-, fluoroalkyl-, fluoroaryl-) substituted thiazolyl, imidazolyl, alkyl-(alkoxy-, aryl-, fluoroalkyl-, fluoroaryl-)substituted imidazolyl, pyrazinyl, alkyl-(alkoxy-, aryl-, fluoroalkyl-, fluoroaryl-) substituted pyrazinyl, benzooxadizolyl, alkyl-(alkoxy-, aryl-, fluoroalkyl-, fluoroaryl-)substituted benzooxadizolyl, benzothiadizolyl, alkyl-(alkoxy-, aryl-, fluoroalkyl-, fluoroaryl-)substituted benzothiadizolyl, fluorenyl, alkyl-(alkoxy-, aryl-, fluoroalkyl-, fluoroaryl-)substituted fluorenyl, triphenylaminyl-substituted fluorenyl, diphenylaminyl-substituted fluorenyl, alkyl-substituted carbazolyl, alkyl-substituted triphenylaminyl and alkyl-substituted thiophenyl. As exemplary embodiments, alkyl substituted phenyl can include 2-alkylphenyl, 3-alkylphenyl, 4-alkylphenyl, 2,4-dialkylphenyl, 3,5-dialkylphenyl, 3,4-dialkylphenyl; alkyl-substituted fluorenyl can include 9,9-dialkyl-substituted fluorenyl, 7-alkyl-9,9-dialkyl-substituted fluorenyl, 6-alkyl-9,9-dialkyl-substituted fluorenyl, 7-triphenylaminyl-9,9-dialkyl-substituted fluorenyl and 7-diphenylaminyl-9,9-dialkyl-substituted fluorenyl; alkyl-substituted carbazolyl can include N-alkyl-substituted carbazolyl, 6-alkyl-substituted carbazolyl and 7-alkyl-substituted carbazolyl; alkyl-substituted triphenylaminyl can include 4'-alkyl-substituted triphenylaminyl, 3'-alkyl-substituted triphenylaminyl, 3',4'-dialkyl-substituted triphenylaminyl and 4',4"-alkyl-substituted triphenylaminyl; alkyl-substituted thiophenyl can include 2-alkylthiophenyl, 3-alkylthiophenyl, and 4-alkylthiophenyl, N-dialkyl-4-phenyl, N-diphenyl-4-phenyl, and N-dialkoxyphenyl-4-phenyl. The narrow-band monomer can be integrated into a backbone of the polymer (e.g., copolymerized in the polymer) and/or covalently attached to the backbone, a terminus, or a sidechain of the polymer) through at least one attachment to $R^{1A}$, $R^{1B}$, $R^{2A}$, $R^{2B}$, $R^{3A}$, $R^{3B}$, $R^{4A}$, $R^{4B}$, $R^{5A}$, $R^{5B}$, $R^{6A}$, $R^{6B}$ or a combination thereof.

In some embodiments, the chromophoric polymer dots of the present invention can include a polymer that includes a narrow-band monomer having the structure of Formula (IX):

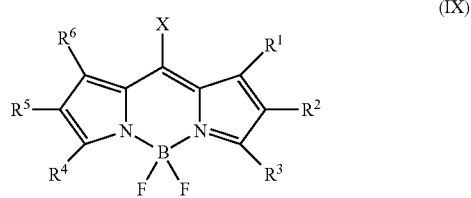

(IX)

wherein X has the structure of any one of Formulae (X), (XI), (XII), or (XIII) or their derivatives:

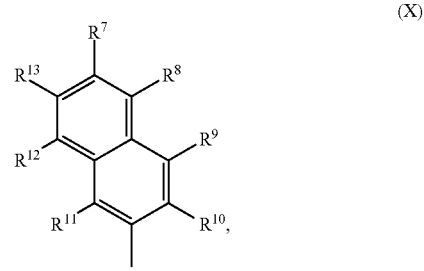

(X)

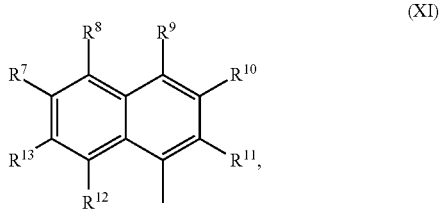

(XI)

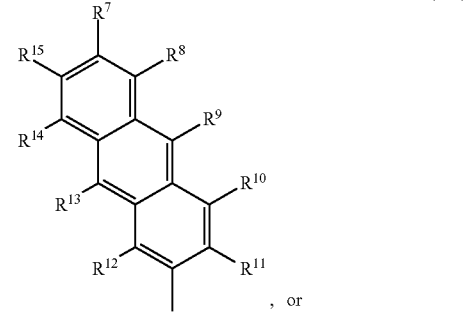

(XII)

, or

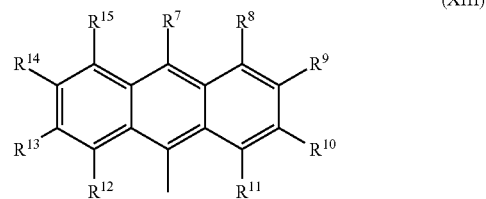

(XIII)

and wherein each of $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$ and $R^{15}$ in Formulae (X), (XI), (XII), and (XIII) is independently selected from the group consisting of hydrogen (H), deuterium (D), halogen, direct or branched alkyl, heteroalkyl, heterocycloalkyl, heterocycloalkylene, alkoxy, aryl, hydroxyl, cyano, nitro, ether and its derivatives, ester and its derivatives, alkyl ketone, alkylester, arylester, alkynyl, alkyl amine, fluoroalkyl, fluoroaryl, and polyalkalene (e.g., mehtoxyethoxyethoxy, ethoxyethoxy, and $(OCH_2CH_2)_nOH$, n=1-50), phenyl, alkyl-(alkoxy-, aryl-, fluoroalkyl-, fluoroaryl-)substituted phenyl, pyridyl, alkyl-(alkoxy-, aryl-, fluoroalkyl-, fluoroaryl-)substituted pyridyl, bipyridyl, alkyl-(alkoxy-, aryl-, fluoroalkyl-, fluoroaryl-)substituted bipyridyl tripyridyl, alkyl-(alkoxy-, aryl-, fluoroalkyl-, fluoroaryl-) substituted tripyridyl, furyl, alkyl-(alkoxy-, aryl-, fluoroalkyl-, fluoroaryl-)substituted furyl, thienyl, alkyl-(alkoxy-, aryl-, fluoroalkyl-, fluoroaryl-)substituted thienyl, pyrrolyl, alkyl-(alkoxy-, aryl-, fluoroalkyl-, fluoroaryl-)substituted pyrrolyl, pyrazolyl, alkyl-(alkoxy-, aryl-, fluoroalkyl-, fluoroaryl-)substituted pyrazolyl, oxazolyl, alkyl-(alkoxy-, aryl-, fluoroalkyl-, fluoroaryl-)substituted oxazolyl, thiazolyl, alkyl-(alkoxy-, aryl-, fluoroalkyl-, fluoroaryl-) substituted thiazolyl, imidazolyl, alkyl-(alkoxy-, aryl-, fluoroalkyl-, fluoroaryl-)substituted imidazolyl, pyrazinyl, alkyl-(alkoxy-, aryl-, fluoroalkyl-, fluoroaryl-) substituted pyrazinyl, benzooxadizolyl, alkyl-(alkoxy-, aryl-, fluoroalkyl-, fluoroaryl-)substituted benzooxadizolyl, benzothiadizolyl, alkyl-(alkoxy-, aryl-, fluoroalkyl-, fluoroaryl-)substituted benzothiadizolyl, fluorenyl, alkyl-(alkoxy-, aryl-, fluoroalkyl-, fluoroaryl-)substituted fluorenyl, triphenylaminyl-substituted fluorenyl, diphenylaminyl-substituted fluorenyl, alkyl-substituted carbazolyl, alkyl-substituted triphenylaminyl and alkyl-substituted thiophenyl. As exemplary embodiments, alkyl substituted phenyl can include 2-alkylphenyl, 3-alkylphenyl, 4-alkylphenyl, 2,4-dialkylphenyl, 3,5-dialkylphenyl, 3,4-dialkylphenyl; alkyl-substituted fluorenyl can include 9,9-dialkyl-substituted fluorenyl, 7-alkyl-9,9-dialkyl-substituted fluorenyl, 6-alkyl-9,9-dialkyl-substituted fluorenyl, 7-triphenylaminyl-9,9-dialkyl-substituted fluorenyl and 7-diphenylaminyl-9,9-dialkyl-substituted fluorenyl; alkyl-substituted carbazolyl can include N-alkyl-substituted carbazolyl, 6-alkyl-substituted carbazolyl and 7-alkyl-substituted carbazolyl; alkyl-substituted triphenylaminyl can include 4'-alkyl-substituted triphenylaminyl, 3'-alkyl-substituted triphenylaminyl, 3',4'-dialkyl-substituted triphenylaminyl and 4',4"-alkyl-substituted triphenylaminyl; alkyl-substituted thiophenyl can include 2-alkylthiophenyl, 3-alkylthiophenyl, and 4-alkylthiophenyl, N-dialkyl-4-phenyl, N-diphenyl-4-phenyl, and N-dialkoxyphenyl-4-phenyl. When X represents naphthalene and its derivatives, the narrow-band monomer can be integrated into a backbone (e.g., polymerized in the polymer) and/or covalently attached to the backbone, a terminus, or a sidechain of the polymer) of the polymer through at least one attachment to $R^7$, $R^8$, $R^9$, $R^{10}$, $R^{11}$, $R^{12}$ or a combination thereof. When X represents anthracene and its derivatives, the narrow-band monomer can be integrated into a backbone of the polymer and/or covalently attached to the backbone, a terminus, or a sidechain of the polymer through at least one attachment to $R^7$, $R^8$, $R^9$, $R^{10}$, $R^{11}$, $R^{12}$, $R^{13}$, $R^{14}$, $R^{15}$ or a combination thereof.

A wide variety of polymer dots can be used, such as the examples described herein as well as others that are disclosed, e.g., in WO2011/057295 and WO2013/101902, each of which is incorporated by reference herein it its entirety and specifically with regard to the particular Pdot compositions and the respective methods of making them as described therein. As provided, e.g., in WO2011/057295, the polymers in the polymer dots can be physically blended or chemically bonded (or chemically crosslinked). For example, the physically blended polymer dots can include polymers that are blended in the polymer dot and held together by non-covalent interactions. Chemically bonded polymer dots can include polymers that are covalently attached to each other in the polymer dot. The chemically bonded polymers can be covalently attached to each other prior to formation of the polymer dots.

For example, the polymer dots can include those that are directly functionalized and/or have low density functionalization.

Functionalized Polymer Dots

In various aspects, the present disclosure provides for the use of "functionalized" polymer dots, and particularly as a means for modifying a surface of the Pdot. As used herein, the term "functionalized" in the context of Pdots refers to Pdots that are linked (e.g., covalently bonded) to one or more functional groups. As used herein, the term "functional group" refers to any chemical unit that can be attached, such as by any stable physical or chemical association, to the chromophoric polymer, thereby altering the surface of the Pdot, e.g., rendering the surface available for conjugation (e.g., bioconjugation). The functional group can be covalently linked to a backbone, side chain, or one of the terminating units of the chromophoric polymer. The functional group can be, without limitation, any the following: a aldehyde, alkene, alkyl, alkyne, strained alkyne, amino, azido, carbonyl, carboxyl, cyano, cyclooctyne, dieno, ester, succinimidyl ester, haloalkyl, hydroxyl, imido, ketone, maleimido, mercapto, phosphate, phosphine, sulfate, sulfonate, substituted derivatives thereof, or a combination thereof. In general, any other functional groups that are suitable for bioconjugation may be used. Such functional groups could be found by one of ordinary skill in the art, for example in Bioconjugate Techniques (Academic Press, New York, 1996 or later versions), which is herein incorporated by reference in its entirety for all purposes.

In some aspects, functional groups of the present disclosure are selected from aldehyde, alkene, alkyl, alkyne, strained alkyne, amino, azido, carbonyl, carboxyl, cyano, cyclooctyne, dieno, ester, succinimidyl ester, haloalkyl, hydroxyl, imido, ketone, maleimido, mercapto, phosphate, phosphine, sulfate, sulfonate, substituted derivatives thereof, or a combination thereof.

In some aspects, methods, systems, compositions and kits are provided for the use of Pdots that have been functionalized. According to the present disclosure, Pdots can be functionalized in any manner that renders them suitable for further modification, e.g., bioconjugation, or for subsequent use in the detection of proteins or peptides. For example, a functional group can be linked (e.g., covalently bonded) to the backbone, the side chain, or one of the terminal units of a chromophoric polymer. In some aspects, a monovalent polymer dot can include a single polymer molecule that includes only one functional group, e.g., at one of two terminal units of the single linear polymer molecule. A bivalent polymer dot can include a single polymer molecule that includes two functional groups, e.g., at each of the two terminal units of the single linear polymer molecule. A trivalent polymer dot can include a single polymer molecule that includes three functional groups, e.g., attachment of functional groups only to the three terminal units of a three-arm branched polymer. Similarly, branched polymer can be used in preparing other multivalent polymer dots, e.g., that have functional groups attached at the terminal units of four-arm, five-arm, six-arm, and branched polymers with higher numbers of branches.

In some aspects, advantages can arise from using polymer dots that include a single polymer molecule having at least one functional group at a terminal unit. For example, the attachment of only one functional group to a terminal unit of a chromophoric polymer can be well controlled in polymer synthesis. For example, a chemical unit comprising a functional group can serve as a polymerization initiator as well as a growth catalyst in polymer synthesis, and in this way each polymer molecule includes just one functional group at the terminus. Attachment of functional groups only to the two terminal units of a linear chromophoric polymer can also be well controlled in polymer synthesis. For example, a chemical unit comprising a functional group can be used as a capping agent to terminate the polymer growth in polymer synthesis, thereby resulting in each linear polymer molecule including only two functional groups in the two terminal units. Similarly, the attachment of functional groups for multivalent polymer dots can be well controlled in polymer synthesis, e.g., functional groups can only be added to the three terminal units of a three-arm branched polymer.

In various aspects, the polymer dot comprises a functional group attached to the polymer dot. In certain aspects, the functional group is selected from a hydrophobic functional group, a hydrophilic functional group, or a combination thereof. In some aspects, the functional group is suitable for bioconjugation.

In certain aspects, the functional group is selected from aldehyde, alkene, alkyl, alkyne, strained alkyne, amino, azido, carbonyl, carboxyl, cyano, cyclooctyne, dieno, ester, succinimidyl ester, haloalkyl, hydroxyl, imido, ketone, maleimido, mercapto, phosphate, phosphine, sulfate, sulfonate, or a combination thereof.

In various aspects, the biomolecule is a protein. In further aspects, the biomolecule is an antibody or an avidin.

Polyelectrolyte-Coated Polymer Dots

The present disclosure provides methods, compositions, kits and systems for using Pdots to detect and measure proteins, e.g., by performing a Western blot analysis. In some aspects, polymer dots that have a polyelectrolyte coating can be used. Advantageously, a polyelectrolyte coating can, e.g., improve the colloidal stability of polymer dots in solutions that have high ionic strength, contain bivalent metal ions, or both. The improved colloidal stability as compared to some polymer dots without the polyelectrolyte coating. e.g., can allow polymer dots to be used in an assay without losing their functionality. In certain aspects, the compositional makeup of the polyelectrolyte coating can be tailored to reduce or eliminate aggregation of the polymer dots in solution, e.g., high ionic strength solutions. In addition, under certain conditions, ions (e.g., bivalent ions) in a solution can chelate groups on the surface of polymer dots, thereby affecting aggregation properties. In some aspects, polyelectrolyte coatings are used to reduce or eliminate aggregation of the polymer dots in solution.

In further aspects, the polymer dot is surrounded by a polyelectrolyte coating. In yet further aspects, the polyelectrolyte coating comprises a polyelectrolyte selected from the group consisting of poly(styrene sulfonate), polyphosphate, polyacrylates, polymethacrylates, polyacrylate-co-maleate, polyacrylamide, chitosan, polysaccharide, polylysine, polyhistidine, and polypeptide.

In certain aspects, the polyelectrolyte coating comprises a polyelectrolyte polymer, wherein each repeating unit of the polyelectrolyte polymer comprises a charge group selected from the group consisting of carboxyl, sulfonate, phosphate, amino, hydroxyl, and mercapto.

The polyelectrolyte coatings can have a layer thickness ranging from about two to four nanometers, thereby adding about four to eight nanometers to the diameter of the nanoparticle including the polymer dot and the polyelectrolyte coating.

The polyelectrolytes in the coating can form on the surface of the polymer dots in a variety of ways. For example, if one type of polyelectrolyte is used, the polyelectrolyte polymer molecules can physically blend together to form the coating. If two or more types of polyelectrolytes are used, the polyelectrolyte polymer molecules can physically blend together to form the coating or, in some aspects, the different polyelectrolytes may form regions (or rafts) on the surface of the nanoparticle. In some aspects, the polyelectrolytes can be chemically crosslinked. For example, some or all of the polyelectrolytes in the coating can be chemically crosslinked using any crosslinking reaction generally well known in the art. The polyelectrolytes may also be chemically crosslinked with the condensed polymer(s) forming the polymer dot. In some aspects, the coating can include more than one layer of polyelectrolytes. For example, the coating can include two layers of polyelectrolytes, three layers of polyelectrolytes, or more layers of polyelectrolytes. The polyelectrolytes in the layers can include the same or different types of polyelectrolytes.

As referred to herein, "polyelectrolytes" can include, e.g., polymers whose repeating units bear an electrolyte group having a charge. In some aspects, the polyelectrolytes can include polymers in which all the repeating units along the polymer bear an electrolyte group. In certain aspects, some of the repeating units of the polymer bear an electrolyte group. For example, polyelectrolytes of the present invention can include polymers in which at least 99%, 95%, 90%, 85%, 80%, 75%, 70%, 65%, 60%, 55%, 50%, 45%, 40%, 35%, 30%, 25%, 20%, 15%, 10%, 5%, or 1% of the repeating units in the polymer bear an electrolyte group. In some aspects, polyelectrolytes of the present invention can include polymers in which at least 99%, 95%, 90%, 85%, or 80.%0 of the repeating units in the polymer bear an electrolyte group.

In some aspects, the polyelectrolytes can include at least one type of electrolyte group. For example, the polyelectrolytes can include only one type of electrolyte group, or two or more types of electrolyte groups. The various electrolyte groups described herein can be included in a variety of different types of polyelectrolytes. Example polyelectrolytes in the present invention can include, but are not limited to, poly(styrene sulfonate), polyphosphate, polyacrylate, polymethacrylate, polyacrylate-co-maleate, polyacrylamide, chitosan, polysaccharide, polylysine, polyhistidine, and polypeptide. The electrolyte group described herein can be included in the polymer backbone, included in side chains attached to the polymer backbone, and/or included in a group that is attached to a side chain of a polymer.

A wide variety of electrolyte groups can be used in the present invention. Generally, any group that generates a charge under certain conditions can be used for the polyelectrolytes. For example, the electrolyte group can include an anion or a cation. In some aspects, the electrolyte group can include one anion or one cation. Alternatively, the electrolyte group can include more than one anion and/or cation such that the electrolyte group includes an overall negative or positive charge. The charge on the electrolyte groups can be a permanent charge or a charge generated according to a specific pH of a solution (e.g., a hydrogen can dissociate to form the charged electrolyte group). In some aspects, the electrolyte group can be a salt (e.g., neutralized with a counterion) prior to being dissolved in an aqueous solution. In some aspects, the electrolyte groups can include, but are not limited to, a carboxyl group, a sulfonate group, a phosphate group, an amino, a hydroxyl group, and a mercapto group. In some aspects, the charges of the electrolyte groups can be generated depending on acidic or basic solution characteristics. For example, a carboxyl group, sulfonate group, phosphate group, hydroxyl group, or mercapto group can be negatively charged, e.g., according to a pH of the solution and the pKa of the respective electrolyte group. In aqueous solutions, the electrolyte groups on polymers can dissociate to form charged groups and thereby making the polymers charged, forming the polyelectrolyte. In some aspects, the electrolyte groups can be substituted with substituents to place a permanent charge on the electrolyte group. For example, an amino group can include a quaternary ammonium cation that has a permanent positive charge. Substituents for the electrolyte groups can be varied, such as alkyl, aryl, CN, amino, sulfide, aldehyde, ester, ether, acid, hydroxyl or halide. In certain aspects, the substituents on the electrolyte groups can provide the charge to the electrolyte.

One aspect of the present invention includes modifying the zeta potential of the polymer dots by providing a polyelectrolyte coating. This coating can be used to modify, e.g., the surface charge of the nanoparticles and prevent aggregation in solutions. Depending on the solution, the zeta potential can be tailored to prevent aggregation. In some aspects, zeta potential is a parameter to evaluate whether the particles dispersed in a solution can resist aggregation. For example, particles (e.g., polymer dots coated with polyelectrolytes) will be stable (e.g., resist aggregation) when the particles have a zeta potential more positive than +30 mV or more negative than −30 mV. Higher value zeta potentials can provide more stability against aggregation. For example, a dispersion of particles with +/−60 mV can provide excellent stability. Depending on the selected polyelectrolyte(s) described herein, the present invention includes particle dispersions (e.g., polymer dots having a polyelectrolyte coating) having zeta potentials that are more positive than about +30 mV, more positive than about +40 mV, more positive than about +50 mV, or move positive than about +60 mV. The present invention includes particle dispersions (e.g., polymer dots having a polyelectrolyte coating) having zeta potentials that are more negative than about −30 mV, more negative than about −40 mV, more negative than about −50 mV, or move negative than about −60 mV. The particles having a polymer dot with a polyelectrolyte coating can be prepared using the methods described herein for the wide variety of polyelectrolytes. The zeta potential of particle dispersions can then be determined using a variety of techniques, such as by using instruments designed to measure zeta potential, e.g., by a Malvern Zetasizer.

In certain aspects, the present invention includes nanoparticles that include a polymer dot having a coating including more than one polyelectrolyte polymer. For example, the coatings can include two different polyelectrolytes, three different polyelectrolytes, four different polyelectrolytes, or more and at any desired ratio.

Bioconjugates of Polymer Dots

In various aspects, the polymer dots of the present disclosure can be bioconjugated to facilitate the detection of proteins or peptides. In some aspects, methods, systems, compositions and kits are provided for the use of Pdots conjugated to biomolecules, such as for example, functionalization of Pdots wherein the biomolecule is attached to the Pdot either directly or indirectly by functional groups.

The term "biomolecule" is used to describe a synthetic or naturally occurring protein, glycoprotein, peptide, amino acid, metabolite, drug, toxin, nuclear acid, nucleotide, carbohydrate, sugar, lipid, fatty acid and the like. Pdots conjugated to biomolecules are sometimes referred to herein as "bioconjugates." Bioconjugates can also include functionalized chromophoric polymer dots associated with biological particles such as viruses, bacteria, cells, and naturally occurring or synthetic vesicles such as liposomes. The functionalized chromophoric polymer dots can include one or more functional groups that are formed from the chromophoric polymer with one or two terminating functional groups, or low density side-chain functional groups.

In certain aspects, the bioconjugates comprise a monovalent chromophoric polymer dot and a biomolecule, wherein the biomolecule is attached to the polymer dot either directly or indirectly by a functional group. The bioconjugates can also comprise monovalent chromophoric polymer dots associated with biological particles such as viruses, bacteria, cells, and naturally occurring or synthetic vesicles such as liposomes.

In some aspects of the present disclosure, the biomolecule is attached to the functional group of a monovalent chromophoric polymer dot via a covalent bond. For example, if the functional group of the polymer dot is a carboxyl group, a protein biomolecule can be directly attached to the polymer dot by cross-linking the carboxyl group with an amine group of the protein molecule.

In various aspects of the present disclosure cross-linking agents can be utilized to facilitate bioconjugation of Pdots. As used herein, the term "cross-linking agent" is used to describe a compound or moiety that is capable of forming a chemical bond between molecular groups on similar or dissimilar molecules so as to covalently bond together the molecules. Examples of common cross-linking agents are known in the art. See, for example, Bioconjugate Techniques (Academic Press, New York, 1996 or later versions). Indirect attachment of the biomolecule to monovalent chromophoric polymer dots can occur through the use of "linker" molecules, for example, avidin, streptavidin, neutravidin, biotin or a like molecule.

In some aspects, methods, systems, compositions and kits are provided for analysis of a target molecule (e.g., a protein) using polymer dots conjugated to biomolecules that specifically bind to the target.

In some aspects, fluorescent Pdots are conjugated to one or more molecules that provide a function or other benefit, including without limitation, binding affinity for a target molecule.

In some aspects, the target molecule is a protein of interest, and the biomolecule conjugated to a Pdot is a primary antibody that specifically binds to the target protein.

In other aspects, the target molecule is a protein of interest bound to a primary antibody for said protein, and the biomolecule conjugated to a Pdot is a secondary antibody that specifically binds to the primary antibody.

In other aspects, the target molecule is a biotinylated protein of interest, and the biomolecule conjugated to a Pdot is an avidin (e.g., streptavidin) that specifically binds to the biotinylated protein.

As used herein, the term "biotin" refers to any one of a variety of biotin derivatives and analogs that are effective in avidin binding. Suitable biotin moieties include those moieties that enable the biotinylated peptide fragment to be isolated by avidin and related avidin proteins. Representative biotin moieties include biotin derivatives such as iminobiotin, biocytin, and caproylamidobiotin, and biotin analogs such as desthiobiotin and biotin sulfone.

As used herein, the term "avidin" refers to any biotin-binding protein other than an immunoglobulin that binds biotin including both natural proteins and recombinant and genetically engineered proteins. The term includes the two common biotin-binding proteins known as "egg white" or "avian" avidin and "streptavidin." Egg white or avian avidin, commonly referred to simply as avidin, is a protein that is a constituent of egg white and forms a noncovalent complex with biotin. Streptavidin is an avidin protein isolated from the actinobacterium *Streptomyces avidinii* and also forms a noncovalent complex with biotin. Other bacterial sources of biotin binding proteins are also known. Both egg white avidin and streptavidin are tetrameric proteins in which the biotin binding sites are arranged in pairs on opposite faces of the avidin molecule. The term also refers to avidin derivatives including succinyl avidin, ferritin avidin, enzyme avidin, and crosslinked avidin.

In some aspects, fluorescent Pdots may be conjugated to one or more molecules that alter other properties of the Pdots, such as their size, fluorescence, hydrophobicity, nonspecific binding or adsorption properties, and the like.

In some aspects, conjugation of biomolecules to Pdots can include attachment of a functional group, including but not limited to attachment of carboxyl groups to Pdots. In some aspects, carboxyl groups can be reacted to N-hydroxysuccinimide (NHS) in the presence of a carbodiimide such as 1-ethyl-3-[3-dimethylaminopropyl]carbodiimide hydrochloride (EDC) to produce amine-reactive esters of carboxylate groups for crosslinking with primary amine groups present on certain biomolecules.

In some aspects, carboxylated Pdots are conjugated to a biomolecule, such as a protein, by mixing of the Pdots and the biomolecules, e.g., in a HEPES buffer (20 mM, pH=7.4) solution containing 0.1% PEG (MW3350). Formation of a peptide bond between the carboxyl groups on Pdots and the amine groups of the biomolecule can be catalyzed by EDC. However, due to the intrinsically hydrophobic nature of the Pdots, biomolecules tend to nonspecifically adsorb onto the particle surface. In some aspects, Triton X-100 and/or bovine serum albumin (BSA) are introduced to reduce non-specific adsorption of a biomolecule onto the surface of a Pdot.

In addition to the examples described herein, in some aspects other strategies and methods for conjugation of biomolecules to Pdots can be used, including those disclosed, e.g., in WO2011/057295 and WO2013/101902. Other strategies and methods for conjugation of biomolecules to Pdots can be found by one of ordinary skill in the art, for example in Bioconjugate Techniques (Academic Press, New York, 1996 or later versions).

Stability of Polymer Dots

The present disclosure also provides compositions and methods suitable for producing and maintaining stable populations of Pdots for use according to the present methods. The presently described Pdots can be prepared for use in compositions and kits for use with Western blot analysis. In some aspects, populations of Pdots can be prepared in a stable form such that they can be stored for a period of time before use in a Western blot assay.

As used herein, the term "stable," can refer to chromophoric polymer dots that do not aggregate and/or change substantially in size (as measured by electron microscopy, atomic force microscopy, or dynamic light scattering) when stored in an appropriate aqueous solution for an extended period of time. Aggregation or a change substantially in size of the polymer dots can, for example, be characterized as an increasing number of aggregates including more than one polymer dot. Aggregates can be detected visually by the eye, with imaging techniques, such as electron microscopy or atomic for microscopy, and/or by increased size measurements shown by dynamic light scattering. In some aspects, aggregation can be characterized by at least about a 10% increase, at least about a 25% increase, at least about a 50% increase, at least about a 100% increase, at least about a 500% increase, or at least about a 1000% increase in measured particle diameter as compared to an original measurement of the chromophoric polymer dots. For example, chromophoric polymer dots can measure a median diameter of 15 nm on day one, and then measure a median diameter of 30 nm four months later, thereby showing a 100% increase in measured particle diameter (i.e., exhibiting aggregation).

In certain aspects, the chromophoric polymer dots can be stable when stored in an appropriate aqueous solution for at least about a month, preferably at least about 2 months, more preferably at least about 4 months. In certain aspects, a stable chromophoric nanoparticle will not aggregate or change substantially in size for at least about 1, 2, 3, 4, 5, 6, 7, 8, 9, 10, 11, 12, 13, 14, 15, 16, 17, 18, 19, 20, 21, 22, 23, 24, 30, 36, 42, 48, or more months. In some aspects, a functionalized chromophoric nanoparticle as provided herein will remain stable in an appropriate aqueous solution for at least about 4 months. In other aspects, a functionalized chromophoric nanoparticle as provided herein will remain stable in an appropriate aqueous solution for at least about 6 months. In a yet other aspects, a functionalized chromophoric nanoparticle as provided herein will remain stable in an appropriate aqueous solution for at least about one year.

In some aspects, the term "stable" can refer to a chromophoric polymer dot being resistant to dissociation of polymer molecules or dopants in the polymer dot. For example, chromophoric polymer dots can include several polymer molecules and those polymer molecules can stay in the polymer dot for a period of time before leaching out into solution. Leaching of polymer molecules from polymer dots can be characterized, for example, by decreased photophysical properties of the polymer dots. In some aspects, decreased stability of the chromophoric polymer dots can be characterized by decreasing emission intensity over time at a wavelength corresponding to the polymer dot emission. In certain aspects, degradation of the polymer dots can be detected by increasing emission intensity over time at a particular wavelength corresponding to polymer emission. In addition to measuring polymer emission, the polymer dots can also be designed to incorporate fluorescent dyes that are in solution during nanoparticle formation. As the polymer dots degrade, the dye can leach out and can be detected over time.

Methods for Analysis Using Chromophoric Polymer Dots

The present disclosure provides the use of chromophoric Pdots for the detection of proteins and peptides. In some aspects, the present disclosure relates to the use of bioconjugated Pdots for use in Western blotting assays, including separation and detection of the proteins or peptides of interest.

According to various aspects of the present disclosure, the proteins or peptides can be separated by chromatography, filtration, capillary electrophoresis, precipitation, liquid or other extraction methods, immunoprecipitation, or a combination thereof.

In certain aspects, other protein detection assays can be performed using Pdots, including, but not limited to, immunostaining, spectrophotometry, enzyme-based assays (e.g., ELISA), and combinations thereof.

The present disclosure can be used in association with any assay that includes the detection of a protein or peptide analyte using Pdots. In various aspects, the protein or peptide can be separated from a mixture before detection. The present methods can be used with an immunological method (e.g., an ELISA assay, an RIA assay, an ELI-Spot assay, a flow cytometry assay, an immunohistochemistry assay, a immunostaining, a Western blot analysis, and a protein chip assay), a physical method (e.g., one- or two-dimensional gel electrophoresis assays, a capillary electrophoresis assay, a FRET assay, a chromatographic assay, or a dye-detection assay, a spectrophotometry assay, a precipitation method), or a combination thereof.

In various aspects, prior to detection using Pdots of the present disclosure, proteins or peptides can be separated by a chromatography method, a filtration method, a capillary electrophoresis method, a gel electrophoresis method, a liquid extraction method, a precipitation method, or an immunoprecipitation method. Further, the chromatography method can be reverse phase chromatography.

In various aspects, a plurality of assays can be performed in parallel to improve analysis throughput.

In various aspects, the present disclosure provides methods for performing Western blot analysis, the method comprising: separating proteins with a gel; transferring the separated proteins to a membrane; contacting the membrane having the separated proteins with a solution comprising a polymer dot conjugated to a biomolecule specific to at least some of the separated proteins; and detecting at least one signal from the polymer dots, the at least one signal corresponding to the separated proteins In various aspects, the present disclosure provides methods for detecting proteins or peptides, the method comprising: separating the proteins or peptides from a mixture; contacting the separated proteins or peptides with a solution comprising a polymer dot conjugated to a biomolecule specific to at least some of the separated proteins or peptides; and detecting at least one signal from the polymer dots, the at least one signal corresponding to the separated proteins or peptides.

In some aspects, the present methods quantitate proteins or peptides.

In some aspects, the separating the proteins or peptides comprises a chromatography method, a filtration method, a capillary electrophoresis method, a gel electrophoresis method, a liquid extraction method, a precipitation method, an immunoprecipitation method, or a combination thereof.

In some aspects, the polymer dot comprises a polymer selected from a semiconducting polymer, a non-semiconducting polymer, or a combination thereof.

In some aspects, the polymer dot comprises a polymer selected from a poly((meth)acrylic acid)-based polymer, a polydiene-based polymer, a poly(ethylene oxide)-based polymer, a polyisobutylene-based polymer, a polystyrene-based polymer, a polysiloxane-based polymer, a poly(ferrocenyldimethylsilane)-based polymer, a poly(2-vinyl naphthalene)-based polymer, a poly(vinyl pyridine)-based polymer, a poly(N-methyl vinyl pyridinium iodide)-based polymer, or a poly(vinyl pyrrolidone)-based polymer.

In some aspects, the present disclosure provides for detection of proteins or peptides in conjunction with a Western blot assay. Western blotting is a protein analysis method in which proteins are separated by mass and/or length, typically using sodium dodecyl sulfate-polyacrylamide gel electrophoresis (SDS-PAGE), then transferred onto a membrane composed of, e.g., nitrocellulose or a fluoropolymer such as polyvinylidene fluoride (PVDF), and visualized using a labelling procedure. In the present disclosure, Pdots are shown to provide detection of protein at quantities as low as 50 picograms using Western blot analysis (see e.g., Example 5).

In some aspects, the present disclosure enables ultrasensitive fluorescence imaging of proteins on Western blots using polymer dots. In certain aspects, the bright, compact, and orange-emitting semiconducting polymer dot, CN-PPV, is used.

In certain aspects, proteins or peptides are separated using gel electrophoresis. In further aspects of the present disclosure, proteins and peptides are separated using capillary electrophoresis in which proteins or peptides are separated and labelled within the capillary. The method is similar to that performed in a standard SDS-PAGE separation, however, occurs within the capillary space.

During gel electrophoresis, proteins separate across the gel according to size. A size-range, or "band", can then be transferred from within the gel onto a membrane. In some aspects, proteins or peptides are transferred to a membrane using an electric current to pull proteins from the gel onto the membrane, in a technique known in the art as electroblotting. In other aspects, capillary forces may be used to move proteins from the gel onto a membrane. In other aspects of the disclosure, other methods of transferring proteins from a gel to a membrane can be used.

In some aspects, the proteins are disposed on a nitrocellulose membrane. In other aspects, the proteins are disposed on a membrane composed of a fluoropolymer, e.g., PVDF. Any suitable membrane can be used according to the present disclosure.

In other aspects, methods are provided for ultrasensitive fluorescence imaging of molecules using Pdots in a dot blot assay. In a dot blot assay, the proteins or peptides to be detected are not first separated. Instead, an un-separated sample is applied directly on a membrane as a dot and visualized using a labelling procedure. In the present disclosure, Pdots are shown to provide detection of protein at quantities lower than two picograms using dot blot analysis.

A detection limit at the single-picogram level has been observed with conventional Western blotting. Detection at the 50-picograms level has been observed for transferrin and trypsin inhibitor after SDS-PAGE and transfer onto a PVDF membrane. Among many advantages, the present invention includes methods that do not require any additional equipment or time compared to the conventional procedure with traditional fluorescent probes.

In some aspects of the disclosure, analysis is performed on samples contained within one or more biological cells, tissues, fluids, or other samples. In other aspects, the analysis can be performed on a sample after it has been collected from one or more biological cells, tissues, fluids or other samples. The protein or peptide can optionally be separated by methods such as, e.g., SDS-PAGE, after which the protein or peptide can be detected with a bioconjugated Pdot that is specific for the protein or peptide of interest.

Proteins or peptides can be collected from a tissue, cell, or fluid sample by methods can include, but are not limited to, freezing and thawing, sonication, homogenization by high pressure, filtration, permeabilization, and centrifugation. In some aspects, an collected protein or peptide can also undergo one or more isolation or purification steps prior to analysis.

In some aspects, analysis can be performed on a sample that contains a heterogeneous mix of different proteins. In other aspects, analysis can be performed on a purified protein.

In some aspects, a sample is separated prior to analysis, such as by gel electrophoresis or another method suitable for separating a sample. In some aspects, proteins or peptides are separated based on their mass and/or charge prior to analysis.

In some aspects, Pdots are suspended in a liquid, and this liquid is brought into physical contact with a sample, the sample being either suspended in a second liquid or disposed on a surface. In some aspects, the sample is disposed on a surface which comprises a membrane.

In some aspects, Pdots are disposed on a surface, and this surface is brought into physical contact with a sample, the sample being suspended in a liquid. In some aspects, the surface on which Pdots are disposed comprises a membrane.

In some aspects, an immunoprecipitation assay is performed, in which Pdots are disposed on a surface and brought into physical contact with a protein sample suspended in a liquid. According to this aspect, contact between the protein sample and the corresponding Pdot causes the protein to adhere to the surface via the binding Pdot.

In various aspects, the presently described Pdots will emit fluorescence when properly induced by an excitation source. In certain aspects, the quantity of Pdots present can be determined and subsequently correlated with the quantity of a given analyte of interest, such as e.g., a protein of interest. Thus, the presently described methods utilize an excitation light source to induce Pdot fluorescence, which can then be measured and correlated with sample concentration. In various aspects, electromagnetic radiation (e.g., infrared radiation, visible light, or ultraviolet radiation) is used to trigger electromagnetic emission from Pdots, and the emitted signal can be used to assess the amount of target molecule present in a sample. In some aspects, the source of electromagnetic radiation can comprise a laser, LED, lamp, spectral filter or multichroic mirror. In some embodiments, the light excitation source can be a component of a gel imaging apparatus, a microscope, or other suitable apparatus. The chemical and physical properties of a given Pdot can be adjusted in order to tune the excitation and emission wavelengths, among other optical properties.

In some aspects, the peak wavelength of electromagnetic radiation that induces excitation of a Pdot is between about 200 nm and about 300 nm, about 250 nm and about 350 nm, about 300 nm and about 400 nm, about 350 nm and about 450 nm, between about 400 nm and about 500 nm, about 450 nm and about 550 nm, about 500 nm and about 600 nm, about 550 nm and about 650 nm, about 600 nm and about 700 nm, about 650 nm and about 750 nm, about 700 nm and about 800 nm, about 750 nm and about 850 nm, about 800 nm and about 900 nm, about 850 nm and about 950 nm, or about 900 nm and about 1000 nm. In some cases more than one excitation spectrum may be experienced by a sample, such as in multiplex analyses.

In some aspects, the peak wavelength of the detected signal is between about 200 nm and about 300 nm, about 250 nm and about 350 nm, about 300 nm and about 400 nm, about 350 nm and about 450 nm, between about 400 nm and about 500 nm, about 450 nm and about 550 nm, about 500 nm and about 600 nm, about 550 nm and about 650 nm, about 600 nm and about 700 nm, about 650 nm and about 750 nm, about 700 nm and about 800 nm, about 750 nm and about 850 nm, about 800 nm and about 900 nm, about 850 nm and about 950 nm, about 900 nm and about 1000 nm, about 950 nm and about 1050 nm, about 1000 nm and about 1100 nm, about 1050 nm and about 1150 nm, about 1100 nm and about 1200 nm, about 1150 nm and about 1250 nm, or about 1200 nm and about 1300 nm.

In some aspects, the assay is sensitive enough to detect less than 500 picograms, less than 400 picograms, less than 300 picograms, less than 200 picograms, less than 100 picograms, less than 50 picograms, less than 40 picograms, less than 30 picograms, less than 20 picograms, less than 10 picograms, less than five picograms, less than four picograms, less than three picograms, less than two picograms, or less than one picogram of a target molecule, such as a protein.

Among many advantages, such as improved detection sensitivity and photo-stability, the present invention includes methods that do not require any additional equipment or time compared to the conventional procedure with traditional fluorescent probes.

Western blot analysis using the presently described polymer dots has significant advantages over existing methods, stemming in part from the superior emission properties and specificity of the Pdots. The use of conjugated Pdots provides superior emission properties, such as high brightness for fluorescence-based detection methods, relative to existing methods. In some aspects, the use of conjugated Pdots provides superior specificity for a target molecule of interest, such as for example, proteins or peptides separated by SDS-PAGE.

As used herein, "specificity" refers to a conjugated Pdot having greater binding affinity for its target than it has for other components it is in physical contact with. A conjugated Pdot is specific for its target if the equilibrium constant for the conjugated Pdot and its target is greater than the average of the equilibrium constants for the conjugated Pdot and the other components it is in physical contact with. Greater specificity indicates a greater binding affinity for the target relative to other components, and this yields improvements in detection sensitivity in assays for a target. Advantageously, the present methods exhibit very high specificity for the target molecules of the present disclosure, such as, e.g., proteins or peptides.

In some aspects of the present disclosure, a blocking agent is used to modify non-specific adsorption and/or binding properties of the conjugated polymer dots. In some aspects, the blocking agent competes with the polymer dots for adsorption onto a surface or a membrane, thereby reducing the incidence of non-specific adsorption of the Pdots. In some aspects, the blocking agent competes with the polymer dots for binding of one or more interfering proteins. The interaction of the blocking agent with surfaces, membranes, and proteins reduces the amount of surface, membrane, and protein that is available for the conjugated polymer dots to adsorb or bind to. The blocking agent improves signal-to-noise ratio of Western blot or other protein analysis because it reduces the amount of emission from polymer dots that are not bound to the target protein (i.e., noise) while having a minimal effect on the amount of emission from polymer dots bound to the target protein (i.e., signal).

In some aspects, the blocking agent can comprise an albumin, e.g., bovine serum albumin (BSA). In some aspects, the blocking agent can include a milk-based product, e.g., non-fat dry milk. In some aspects, the blocking agent can include a casein-based product, e.g., I-Block (Life Technologies). In some aspects, the blocking agent can further include a detergent, e.g., Triton X.

In some aspects, the use of conjugated Pdots improves detection sensitivity because of the relatively low levels of non-specific adsorption to surfaces by those Pdots, e.g., to membranes on which a sample is disposed. In certain aspects, non-specific adsorption is minimized by using a blocking agent, which is any agent that blocks non-specific binding that is capable of interfering with the accurate detection of target proteins or peptides with Pdots. For example, blocking agents advantageously block non-specific adsorption of Pdots and/or biomolecules onto surfaces that the Pdots and/or biomolecules can come into physical contact with.

In some aspects, the separation comprises the use of a gel, wherein the gel comprises polyacrylamide, agarose, starch, or a combination thereof. In some aspects, the separation comprises a SDS-PAGE separation. In certain aspects, the method uses a membrane and the membrane comprises nitrocellulose or a fluoropolymer membrane. In further aspects, the fluoropolymer is PVDF.

In certain aspects, the detecting comprises detecting picogram quantities of the separated proteins. In further aspects, the detecting comprises detecting less than two picograms of the separated proteins. In certain aspects, the method further comprises exciting the polymer dot with a source of electromagnetic radiation. In some aspects, the source of electromagnetic radiation comprises a laser, a lamp, an LED, or a combination thereof. In further aspects, the electromagnetic radiation passes through a spectral filter, a multichroic mirror, or a combination thereof, before exciting the polymer dot.

In some aspects, the peak wavelength of electromagnetic radiation exciting the sample is between about 200 nm and about 300 nm, about 250 nm and about 350 nm, about 300 nm and about 400 nm, about 350 nm and about 450 nm, between about 400 nm and about 500 nm, about 450 nm and about 550 nm, about 500 nm and about 600 nm, about 550 nm and about 650 nm, about 600 nm and about 700 nm, about 650 nm and about 750 nm, about 700 nm and about 800 nm, about 750 nm and about 850 nm, about 800 nm and about 900 nm, about 850 nm and about 950 nm, or about 900 nm and about 1000 nm. In some aspects, two or more peak wavelengths of electromagnetic radiation excite the sample.

Compositions and Kits for Analysis Using Chromophoric Polymer Dots

In some aspects of the present disclosure, kits are provided for analysis using polymer dots. In various aspects, each of the compositions provided herein can also be configured for use in a kit. In some aspects, the composition or kit comprises Pdots conjugated to biomolecules for performing an assay. In some aspects, the kit provides an end user with methods and reagents for performing more sensitive assays using conventional lab equipment and procedures.

The test kit may optionally comprise substances for use as standard and/or controls.

In various aspects, the present disclosure provides kits for determining the absolute concentration or the relative concentration, or determining the presence or absence of a target protein or peptide. In some aspects, the present kits can be used to analyze samples from a subject. In some aspects, the kit can be used in conjunction with a separation method, such as e.g., gel electrophoresis, capillary electrophoresis, chromatography, filtration, precipitation, liquid or other extraction methods, immunoprecipitation, or a combination thereof.

In a further embodiment, the kit of the present disclosure can optionally comprise instructions for separating and/or detecting proteins or peptides according to the present disclosure. The instructions can also include instructions for how to use the kit, how to prepare the samples, the kinds of samples to use, how to analyze and interpret the results.

In various aspects, the present disclosure provides compositions and kits comprising conjugated polymer dots for Western blot analysis. In further aspects, the compositions and kits comprise a blocking agent.

In some aspects, the compositions or kits comprise agents that modify properties of an assay.

In some aspects, the compositions or kits comprise blocking agents that block non-specific binding of Pdots and/or biomolecules to components other than the target molecule that can be present in a sample.

In certain aspects, the compositions and kits of the present disclosure have a blocking agent that is capable of modifying the non-specific adsorption properties of the conjugated polymer dots or unconjugated polymer dots. In further aspects, the blocking agent competes with the polymer dots for adsorption onto a surface or a membrane or the blocking agent competes with the polymer dots for binding of one or more biomolecules.

In some aspects, the compositions or kits comprise bovine serum albumin (BSA).

In certain aspects, the compositions and kits of the present disclosure contain polymer dots that comprise a polymer selected from a semiconducting polymer, a non-semiconducting polymer, or a blend thereof.

In some aspects, the polymer dots in the compositions and kits have a critical dimension of less than 30 nm, less than 25 nm, less than 20 nm, less than 15 nm, less than 10 nm or less than 5 nm.

In some aspects, the compositions or kits comprise Pdots that have undergone an intermediate functionalizing step, such as carboxylation.

In certain aspects, the kits of the present disclosure further provide reagents for conjugating the polymer dots to the biomolecules.

In some aspects, the compositions or kits comprise Pdots that have been conjugated to one or more biomolecules that provide a function or other benefit, such as binding affinity for a target molecule.

In some aspects, the compositions and kits of the present disclosure have a conjugation biomolecule that is conjugated to the polymer dots. That conjugation biomolecule can be a protein or other suitable biomolecule. In further aspects, the biomolecule can be an antibody or avidin.

In some aspects, the compositions or kits comprise Pdots conjugated to primary antibodies that specifically bind a target protein. In some aspects, the kit comprises Pdots conjugated to secondary antibodies that specifically bind a target primary antibody. In some aspects, the kit comprises Pdots conjugated to avidins that specifically bind biotin and/or biotinylated targets. In some aspects, the kit comprises Pdots conjugated to one or more molecules that alter other properties of the Pdots, such as their size, fluorescence, hydrophobicity, non-specific binding or adsorption properties, and the like.

In some aspects, the composition or kit comprises reagents configured for an end user to conjugate Pdots to proteins or peptides for use in performing an assay. In some aspects, the kit comprises Pdots (e.g., CN-PPV or BODIPY derivatives as described herein and in WO2013/101902), biomolecules (e.g., streptavidin), PEG, and/or EDL. In other aspects, the kit comprises other Pdots, biomolecules, and reagents configured for an end user to conjugate Pdots to biomolecules for use in performing an assay.

In various aspects, the present disclosure provides compositions comprising conjugated polymer dots for Western blot analysis. In other aspects, the present disclosure provides kits comprising conjugated polymer dots and at least one blocking agent for Western blot analysis. In other aspects, the present disclosure provides kits for performing Western blot analysis, the kit comprising polymer dots, a conjugation biomolecule, and a blocking agent.

In other aspects, the present disclosure provides kits for performing a protein or peptide analysis, the kit comprising polymer dots, a conjugation biomolecule, and a blocking agent. In some aspects, the polymer dots comprise a polymer selected from a semiconducting polymer, a non-semiconducting polymer, or a combination thereof. In further aspects, the polymer dot comprises a BODIPY derivative. In still further aspects, the BODIPY derivative has the structure of Formula (I):

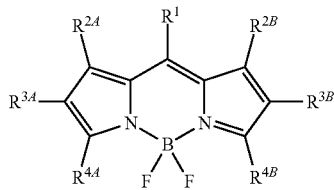

wherein each of $R^1$, $R^{2A}$, $R^{2B}$, $R^{3A}$, $R^{4A}$ and $R^{4B}$ is independently selected from hydrogen, alkyl, aralkyl, aryl, and alkoxy-aryl, and wherein the BODIPY derivative is integrated into the chromophoric polymer by attachment to $R^1$, $R^{2A}$, $R^{2B}$, $R^{3A}$, $R^{4A}$ and $R^{4B}$, or a combination thereof. In certain aspects, the polymer dots comprise a polymer consisting of CN-PPV.

In some aspects, the polymer dots comprises a polymer selected from a poly((meth)acrylic acid)-based polymer, a polydiene-based polymer, a poly(ethylene oxide)-based polymer, a polyisobutylene-based polymer, a polystyrene-based polymer, a polysiloxane-based polymer, a poly(ferrocenyldimethylsilane)-based polymer, a poly(2-vinyl naphthalene)-based polymer, a poly(vinyl pyridine)-based polymer, a poly(N-methyl vinyl pyridinium iodide)-based polymer, or a poly(vinyl pyrrolidone)-based polymer.

In various aspects, the polymer dots comprise a polymer selected from poly(acrylic acid-b-acrylamide), poly(acrylic acid-b-methyl methacrylate), poly(acrylic acid-b-N-isopropylacrylamide), poly(n-butylacrylate-b-acrylic acid), poly(sodium acrylate-b-methyl methacrylate), poly(methacrylic acid-b-neopentyl methacrylate), poly(methyl methacrylate-b-acrylic acid), poly(methyl methacrylate-b-methacrylic acid), poly(methyl methacrylate-b-N,N-dimethyl acrylamide), poly(methyl methacrylate-b-sodium acrylate), poly(methyl methacrylate-b-sodium methacrylate), poly(neopentyl methacrylate-b-methacrylic acid), poly(t-butyl methacrylate-b-ethylene oxide), poly(2-acrylamido-2-methylpropanesulfonic acid-b-acrylic acid), poly(butadiene(1,2 addition)-b-ethylene oxide), poly(butadiene(1,2 addition)-b-methylacrylic acid, poly(butadiene(1,4 addition)-b-acrylic acid), poly(butadiene(1,4 addition)-b-ethylene oxide, poly(butadiene(1,4 addition)-b-sodium acrylate), poly(butadiene (1,4 addition)-b-N-methyl 4-vinyl pyridinium iodide), poly(isoprene-b-ethylene oxide), poly(isoprene-b-ethylene oxide), and poly(isoprene-b-N-methyl 2-vinyl pyridinium iodide), poly(ethylene oxide-b-acrylic acid), poly(ethylene oxide-b-acrylamide), poly(ethylene oxide-b-butylene oxide), poly(ethylene oxide-b-c-caprolactone), poly(ethylene oxide-b-lactide), poly(ethylene oxide-b-lactide), poly (ethylene oxide-b-methacrylic acid), poly(ethylene oxide-b-methyl acrylate), poly(ethylene oxide-b-N-isopropylacrylamide), poly(ethylene oxide-b-methyl methacrylate), poly(ethylene oxide-b-nitrobenzyl methacrylate), poly(ethylene oxide-b-N,N-dimethylaminoethylmethacrylate), poly(ethylene oxide-b-propylene oxide), poly(ethylene oxide-b-t-butyl acrylate), poly(ethylene oxide-b-t-butyl methacrylate), poly(ethylene oxide-b-tetrahydrofurfuryl methacrylate), poly(ethylene oxide-b-2-ethyl oxazoline), poly(ethylene oxide-b-2-hydroxyethyl methacrylate), poly(ethylene oxide-b-2-methyl oxazoline), poly(isobutylene-b-acrylic acid), poly(isobutylene-b-ethylene oxide), poly(isobutylene-b-methacrylic acid), poly(styrene-b-acrylamide), poly(styrene-b-acrylic acid), poly(styrene-b-cesium acrylate), poly(styrene-b-ethylene oxide), poly(styrene-b-ethylene oxide) acid cleavable at the block junction, poly(styrene-b-methacrylic acid), poly(4-styrenesulfonic acid-b-ethylene oxide), poly(styrenesulfonic acid-b-methylbutylene), poly(styrene-b-N,N-dimethylacrylamide), poly(styrene-b-N-isopropyl acrylamide), poly(styrene-b-N-methyl 2-vinyl pyridinium iodide), poly(styrene-b-N-methyl-4-vinyl pyridinium iodide), poly(styrene-b-propylacrylic acid), poly(styrene-b-sodium acrylate) poly(styrene-b-sodium methacrylate), polyp-chloromethyl styrene-b-acrylamide), poly(styrene-co-p-chloromethyl styrene-b-acrylamide), poly(styrene-co-p-chloromethyl styrene-b-acrylic acid), poly(styrene-b-methylbutylene-co-isoprene sulfonate), poly(dimethylsiloxane-b-acrylic acid), poly(dimethylsiloxane-b-ethylene oxide), poly(dimethylsiloxane-b-methacrylic acid), poly(ferrocenyldimethylsilane-b-ethylene oxide), poly(2-vinyl naphthalene-b-acrylic acid), poly(2-vinyl pyridine-b-ethylene oxide), poly(2-vinyl pyridine-b-methyl acrylic acid), poly(N-methyl 2-vinyl pyridinium iodide-b-ethylene oxide), poly(N-methyl 4-vinyl pyridinium iodide-b-methyl methacrylate), poly(4-vinyl pyridine-b-ethylene oxide), poly(vinyl pyrrolidone-b-D/L-lactide), PDHF, PFO, PFPV, PFBT, PFTBT, MEH-PPV, CN-PPV, PPE, or a combination thereof.

In some aspects, the polymer dot is surrounded by a polyelectrolyte coating. In some aspects, the polyelectrolyte coating comprises a polyelectrolyte selected from the group consisting of poly(styrene sulfonate), polyphosphate, polyacrylates, polymethacrylates, polyacrylate-co-maleate, polyacrylamide, chitosan, polysaccharide, polylysine, polyhistidine, and polypeptide. In further aspects, the polyelectrolyte coating comprises a polyelectrolyte polymer, wherein each repeating unit of the polyelectrolyte polymer comprises a charge group selected from the group consisting of carboxyl, sulfonate, phosphate, amino, hydroxyl, and mercapto.

In some aspects, the polymer dots comprise a functional group attached to the polymer dot. In certain aspects, the functional group is selected from a hydrophobic functional group, a hydrophilic functional group, or a combination thereof. In various aspects, the functional group is suitable for bioconjugation. In some aspects, the functional group is selected from aldehyde, alkene, alkyl, alkyne, strained alkyne, amino, azido, carbonyl, carboxyl, cyano, cyclooctyne, dieno, ester, succinimidyl ester, haloalkyl, hydroxyl, imido, ketone, maleimido, mercapto, phosphate, phosphine, sulfate, sulfonate, or a combination thereof. In some aspects, the conjugation biomolecule is conjugated to the polymer dots. In further aspects, the biomolecule is a protein. In still further aspects, the biomolecule is an antibody or an avidin.

In some aspects, the blocking agent modifies the non-specific adsorption properties of the conjugated polymer dots or wherein the blocking agent modifies the non-specific adsorption properties of the polymer dots. In further aspects, the blocking agent competes with the polymer dots for adsorption onto a surface or a membrane. In yet further aspects, the blocking agent competes with the polymer dots for binding of one or more biomolecules.

In some aspects, the kits further comprise reagents for conjugating the polymer dots to the biomolecules.

In certain aspects, the kits comprise membranes selected from a nitrocellulose or a fluoropolymer membrane. In further aspects, the fluoropolymer is PVDF.

In some aspects, the kits further comprise PEG, EDL, or a combination thereof.

Systems for Analysis Using Chromophoric Polymer Dots

In some aspects of the present disclosure, systems are provided for performing Western blot analysis using polymer dots. In various aspects, the systems can comprise Pdots conjugated to biomolecules for performing an assay, a gel, a separation platform, a source of electromagnetic radiation, a detector, and a computer comprising a memory device with executable instructions stored thereon, the instructions, when executed by a processor, cause the processor to: operate the detector to acquire an image, store the image, and analyze the image to detect and/or determine the concentration of a target protein or peptide of interest. In some aspects, the separation platform comprises gel electrophoresis or capillary electrophoresis. In some aspects, the system further comprises a membrane. In some aspects, the intensity of a signal emitted by the Pdots is used to detect a protein or peptide and/or calculate the concentration of a protein or peptide.

In some aspects, the system provides a gel and an electrophoresis platform for separating the protein sample according to protein mass or other property separable by electrophoresis. The gel can include gel composed of polyacrylamide, nitrocellulose, starch, or a combination thereof. The gel can further include gel composed of SDS, urea, beta-mercaptoethanol, dithiothreitol, DMSO, glyoxal, methylmercury hydroxide, or a combination thereof. The electrophoresis platform holds the gel, and a buffer solution in which the gel is immersed. The electrophoresis platform can be made out of an insulating material, such a non-conductive plastic. The electrophoresis platform can include, or be configured to connect to, a source of electrical current for generating an electromotive force that can be used to move the proteins through the gel matrix, causing the proteins to separate according to protein mass or other separable property.

As described further herein, the signal emitted by Pdots to detect a protein can be generated and analyzed by any suitable manner. In some aspects, the system provides a membrane on which a protein sample and Pdots conjugated to biomolecules that bind a target protein are disposed. The membrane can include a membrane composed of nitrocellulose or a fluoropolymer, e.g., PVDF.

In some aspects, the system provides a source of electromagnetic radiation configured to act as a source of excitation for Pdots bound to a target protein. In some aspects, the source of electromagnetic radiation includes a laser. In some aspects, the peak wavelength emitted by the laser is between about 200 nm and about 300 nm, about 250 nm and about 350 nm, about 300 nm and about 400 nm, about 350 nm and about 450 nm, between about 400 nm and about 500 nm, about 450 nm and about 550 nm, about 500 nm and about 600 nm, about 550 nm and about 650 nm, about 600 nm and about 700 nm, about 650 nm and about 750 nm, about 700 nm and about 800 nm, about 750 nm and about 850 nm, about 800 nm and about 900 nm, about 850 nm and about 950 nm, or about 900 nm and about 1000 nm. In some aspects, two or more lasers having distinct peak wavelengths can be used.

In some aspects, the source of electromagnetic radiation includes a light emitting diode (LED). An LED is a semiconducting light source. When the LED's anode lead has a voltage that is more positive than its cathode lead by at least the LED's forward voltage drop, current flows. Electrons are able to recombine with holes within the device, releasing energy in the form of photons. The color of the light (corresponding to the energy of the photon) is determined by the energy band gap of the semiconductor. In some aspects, the peak wavelength emitted by the LED is between about 200 nm and about 300 nm, about 250 nm and about 350 nm, about 300 nm and about 400 nm, about 350 nm and about 450 nm, between about 400 nm and about 500 nm, about 450 nm and about 550 nm, about 500 nm and about 600 nm, about 550 nm and about 650 nm, about 600 nm and about 700 nm, about 650 nm and about 750 nm, about 700 nm and about 800 nm, about 750 nm and about 850 nm, about 800 nm and about 900 nm, about 850 nm and about 950 nm, or about 900 nm and about 1000 nm. In some aspects, two or more LEDs having distinct peak wavelengths can be used.

In some aspects, the source of electromagnetic radiation includes a lamp. e.g., a mercury lamp, halogen lamp, metal halide lamp, or other suitable lamp. In some aspects, light emitted by the lamp is spectrally filtered by a light filtering apparatus. In some aspects, the light filtering apparatus includes a filter, e.g., a bandpass filter that only allows light wavelengths falling within a certain range to pass through it towards a sample containing Pdots. In some aspects, the light filtering apparatus includes a multichroic mirror that can separate light into distinct spectral components, such that it only allows light wavelengths falling within a certain range to be directed towards a sample containing Pdots.

In some aspects, the longest wavelength that passes through the light filtering apparatus is less than 300 nm, less than 400 nm, less than 500 nm, less than 600 nm, less than 700 nm, less than 800 nm, less than 900 nm, or less than 1000 nm.

In some aspects, the shortest wavelength that passes through the light filtering apparatus is more than 200 nm, more than 300 nm, more than 400 nm, more than 500 nm, more than 600 nm, more than 700 nm, more than 800 nm, or more than 900 nm.

The systems of the present disclosure further include a detector and a computer configured to analyze the signal emitted by the Pdots. The detector can include detectors for analyzing the signal intensity, signal-to-noise ratio, and/or other characteristics of interest. The methods described herein will be generally compatible with any known systems capable of detecting and analyzing optical information such as images.

In some aspects, the system provides a detector that detects one or more signals emitted by Pdots bound to a target protein. In some aspects, the detector is a gel imaging apparatus, such as a GE Typhoon FLA 9000 Gel Imaging Scanner (GE Healthcare, Piscataway, N.J.). In some aspects, the detector includes a microscope, such as an epifluorescence microscope. In some aspects, the detector includes a camera, such as a charge-coupled device (CCD) camera, that can integrate the signal into an image on a digital chip.

In some aspects, the system provides a computer comprising a memory device with executable instructions stored thereon. In some aspects, the instructions, when executed by a processor, cause the processor to: operate the detector to acquire an image, store the image, and analyze the image to detect and/or determine the concentration of a target protein of interest.

Examples of a processor include, but are not limited to, a personal computing device that stores information acquired by a detector, and software running on the personal computing device that processes the information. In other aspects, an information processor or component thereof can be embedded in a detector, such as in a chip embedded in a camera that stores optical information acquired by the camera either permanently or temporarily. In other aspects, an information processor and a detector can be components of a fully integrated device that both acquires and stores signals emitted by the Pdots in an assay, e.g., optical signals.

In some aspects, the system provides a computer-readable storage medium for acquiring, storing and analyzing a signal. The computer-readable storage medium has stored thereon instructions that, when executed by one or more processors of a computer, cause the computer to: operate the detector to acquire an image, store the image, and analyze the image to detect and/or determine the concentration of a target protein of interest.

In yet another aspect, a system is provided for analyzing a signal emitted by Pdots to detect a protein and/or calculate the concentration of a protein. The system includes one or more processors, and a memory device including instructions executable by the one or more processors. When the instructions are executed by the one or more processors, the system at least receives a user input to analyze a signal. The system can be configured to carry out aspects of the methods of the present disclosure, such as measuring the intensity of the signal to determine a concentration of the protein target. The system also provides data to a user. The data provided to the user can include the concentration of one or more proteins.

In some aspects, a computer can be used to perform the methods described herein. In various aspects, a computer can be used to implement any of the systems or methods illustrated and described above. In some aspect, a computer can include a processor that communicates with a number of peripheral subsystems via a bus subsystem. These peripheral subsystems can include a storage subsystem, comprising a memory subsystem and a file storage subsystem, user interface input devices, user interface output devices, and a network interface subsystem.

In some aspects, a bus subsystem provides a mechanism for enabling the various components and subsystems of the computer to communicate with each other as intended. The bus subsystem can include a single bus or multiple busses.

In some aspects, a network interface subsystem provides an interface to other computers and networks. The network interface subsystem can serve as an interface for receiving data from and transmitting data to other systems from a computer. For example, a network interface subsystem can enable a computer to connect to the Internet and facilitate communications using the Internet.

In some aspect, the computer includes user interface input devices such as a keyboard, pointing devices such as a mouse, trackball, touchpad, or graphics tablet, a scanner, a barcode scanner, a touch screen incorporated into the display, audio input devices such as voice recognition systems, microphones, and other types of input devices. In general, use of the term "input device" is intended to include all possible types of devices and mechanisms for inputting information to a computer.

In some aspect, the computer includes user interface output devices such as a display subsystem, a printer, a fax machine, or non-visual displays such as audio output devices, etc. The display subsystem can be a cathode ray tube (CRT), a flat-panel device such as a liquid crystal display (LCD), or a projection device. In general, use of the term "output device" is intended to include all possible types of devices and mechanisms for outputting information from a computer.

In some aspects, the computer includes a storage subsystem that provides a computer-readable storage medium for storing the basic programming and data constructs. In some aspects, the storage subsystem stores software (programs, code modules, instructions) that when executed by a processor provides the functionality of the methods and systems described herein. These software modules or instructions can be executed by one or more processors. A storage subsystem can also provide a repository for storing data used in accordance with the present invention. The storage subsystem can include a memory subsystem and a file/disk storage subsystem.

In some aspects, the computer includes a memory subsystem that can include a number of memories including a main random access memory (RAM) for storage of instructions and data during program execution and a read only memory (ROM) in which fixed instructions are stored. A file storage subsystem provides a non-transitory persistent (non-volatile) storage for program and data files, and can include a hard disk drive, a floppy disk drive along with associated removable media, a Compact Disk Read Only Memory (CD-ROM) drive, an optical drive, removable media cartridges, and other like storage media.

The computer can be of various types including a personal computer, a portable computer, a workstation, a network computer, a mainframe, a kiosk, a server or any other data processing system. Due to the ever-changing nature of computers and networks, the description of computer contained herein is intended only as a specific example for purposes of illustrating the embodiment of the computer. Many other configurations having more or fewer components than the system described herein are possible.

In various aspects, the present disclosure provides systems for assaying a protein or peptide, the system comprising: a polymer dot conjugated to a biomolecule; a protein or peptide separation platform; a source of electromagnetic radiation; a detector; and a computer comprising a memory device with executable instructions stored thereon, the instructions when executed by the processor cause the processor to: operate the detector to acquire an image, store the image, and analyze the image.

In some aspects, the protein or peptide separation platform comprises a gel separation platform or a capillary electrophoresis separation platform.

In various aspects, the present disclosure provides systems for performing Western blot analysis, the system comprising: a polymer dot conjugated to a biomolecule; a gel; an electrophoresis platform; a source of electromagnetic radiation; a detector; and a computer comprising a memory device with executable instructions stored thereon, the instructions when executed by the processor cause the processor to: operate the detector to acquire an image, store the image, and analyze the image.

In certain aspects, the gel comprises a polyacrylamide gel. In further aspects, the membrane comprises nitrocellulose or a fluoropolymer. In yet further aspects, the fluoropolymer is PVDF.

In some aspects, the system's source of electromagnetic radiation comprises a laser, a lamp, an LED, or a combination thereof. In other aspects, the system further comprises a spectral filter, a multichroic mirror, or a combination thereof. In further aspects, the detector comprises a gel imaging apparatus. In yet further aspects, the detector comprises a microscope. In still further aspects, the detector comprises a camera.

All publications, patents, and patent applications mentioned in this specification are herein incorporated by reference to the same extent as if each individual publication, patent, or patent application is specifically and individually indicated to be incorporated by reference.

The specific dimensions of any of the apparatuses, devices, systems, and components thereof, of the present invention can be readily varied depending upon the intended application, as will be apparent to those of skill in the art in view of the disclosure herein. Moreover, it is understood that the examples and embodiments described herein are for illustrative purposes only and that various modifications or changes in light thereof may be suggested to persons skilled in the art and are included within the spirit and purview of this application and scope of the appended claims. Numerous different combinations of embodiments described herein are possible, and such combinations are considered part of the present invention. In addition, all features discussed in connection with any one embodiment herein can be readily adapted for use in other embodiments herein. The use of different terms or reference numerals for similar features in different embodiments does not necessarily imply differences other than those expressly set forth. Accordingly, the present invention is intended to be described solely by reference to the appended claims, and not limited to the embodiments disclosed herein.

Unless otherwise specified, the presently described methods and processes can be performed in any order. For example, a method describing steps (a), (b), and (c) can be performed with step (a) first, followed by step (b), and then step (c). Or, the method can be performed in a different order such as, for example, with step (b) first followed by step (c) and then step (a). Furthermore, those steps can be performed simultaneously or separately unless otherwise specified with particularity.

While preferred aspects of the present disclosure have been shown and described herein, it is to be understood that the disclosure is not limited to the particular aspects of the disclosure described, as variations of the particular aspects can be made and still fall within the scope of the appended claims. It is also to be understood that the terminology employed is for the purpose of describing particular aspects of the disclosure, and is not intended to be limiting. Instead, the scope of the present disclosure is established by the appended claims. In this specification and the appended claims, the singular forms "a," "an" and "the" include plural reference unless the context clearly dictates otherwise.

Where a range of values is provided, it is understood that each intervening value, to the tenth of the unit of the lower limit unless the context clearly dictates otherwise, between the upper and lower limit of that range, and any other stated or intervening value in that stated range, is encompassed within the disclosure provided herein. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the disclosure provided herein.

EXEMPLARY ASPECTS

Example 1

Properties of Fluorescent Polymer Dot-Based Reporters

In this example, Pdot-streptavidin conjugates, made out of a new orange-emitting poly[2-methoxy-5-(2-ethylhexyloxy)-1,4-(1-cyanovinylene-1,4-phenylene)](CN-PPV) polymer, (Ye, F. et al., Chem. Comm., 2012, 48, 1778) were used to visualize proteins labelled with biotin-conjugated antibodies. Low-picogram detection sensitivity was achieved. The fluorescence signal from Pdots bound to proteins remained the same in successive images, even two weeks after the blotting procedure.

To prepare CN-PPV Pdots, CN-PPV (from ADS Dyes Inc.) and poly(styrene-co-maleic anhydride) (PSMA, from Sigma-Aldrich) were each dissolved in tetrahydrofuran (THF) to make one mg/mL stock solutions (1000 ppm). These stock solutions were diluted by putting 125 µL of the CN-PPV stock solution and 25 µL of the stock PSMA solution into a 5 mL aliquot of THF. This mixture was sonicated and quickly injected into 10 mL of water in a bath sonicator, after which the THF was removed under slow nitrogen flow with heating. This nanoprecipitation procedure resulted in the formation of Pdots. 10 mL of the Pdot solution was further concentrated under nitrogen flow with heating to give 5 mL of the final Pdot solution at a concentration of 50 ppm. Before further use, this Pdot solution was passed through 0.2 µm cellulose acetate filter to remove any large aggregates in the solution.

To conjugate Pdots with streptavidin, to this 5 mL of Pdot solution, 100 µL of PEG (5% w/v in water, MW 3350), 100 µL of 1 M HEPES buffer (pH 7.4), 300 µL of streptavidin (1 mg/mL in 20 mM HEPES buffer), and 50 µL of 1-ethyl-3-(3-dimethylaminopropyl) carbodiimide (EDC, from Sigma-Aldrich) (10 mg/mL in water) were added. The solution was mixed on a vortex and further stirred at room temperature for four hours before adding a 100 µL aliquot of 1% w/v bovine serum albumin (BSA, from Sigma-Aldrich) in water. After another 20 min stirring step, sucrose (10% w/v) was added and the solution was concentrated to a 0.5 mL volume by centrifugal filtration (filter MWCO 100,000). Finally, the Pdot-streptavidin conjugates were purified by passing the concentrated solution through a Sephacryl HR-300 gel column, which is equilibrated with 0.1% PEG (w/v) and 20 mM HEPES at pH 7.4. The final solution of Pdot-streptavidin has a concentration of 400 ppm of polymer, which was determined from its UV-visible absorption spectrum.

FIG. 1A shows the structure of CN-PPV polymer and the optical properties of CN-PPV Pdot and CN-PPV-streptavidin Pdot bioconjugates. The CN-PPV Pdot possesses a quantum yield as high as 60% and an absorption cross-section of ~$2.3 \times 10^{-13}$ cm$^2$ for a 10 nm-diameter Pdot. Its fluorescence lifetime is 1.5 ns. The peak emission is located at 595 nm, providing a lower autofluorescence background compared to its blue-emitting analogues.

FIG. 1C shows representative transmission electron microscopy (TEM) images of CN-PPV Pdot and CN-PPV-streptavidin Pdots. FIG. 1D shows their size measured by dynamic light scattering (DLS), demonstrating a ~2-nm increase in diameter after bioconjugation to streptavidin. Based on the ratio of PSMA to streptavidin (1:20 in molarity) and the size of the Pdot, ~5-10 streptavidin molecules per 10 nm-diameter Pdot were estimated. As a comparison, Qdot 605-streptavidin (with a diameter of ~15 nm; quantum yield=30%) was used. Its emission is very close to that of CN-PPV Pdot and with its absorption cross-section of ~2.3×10$^{-15}$ cm$^2$, it can be efficiently excited at 473 nm, which is the excitation wavelength that the fluorescence scanner uses (FIG. 1B).

Example 2

Use of Fluorescent Polymer Dots to Detect a Primary Antibody

This example describes the detection of goat anti-mouse (GAM) IgG using CN-PPV Pdot conjugates. Directly depositing proteins onto the polyvinylidene fluoride membrane (PVDF, from Fisher Scientific) in the form of dot blots permitted a convenient quantitative protein detection test that bypassed the uncertainty associated with the transfer of proteins from a SDS-PAGE gel onto the membrane. Dot blots were used to elucidate the lowest detection limits for the probed proteins.

To further minimize uncertainty associated with the antibody-to-protein binding constants, biotinylated goat anti-mouse (GAM) IgG (from BioLegend) dot blots were visualized with either Qdot 605-streptavidin or CN-PPV Pdot-streptavidin conjugates. To carry out this comparison, biotinylated GAM IgG in TTBS buffer (20 mM Tris, 500 mM NaCl, pH 7.4, 0.05% Tween-20) was diluted to the desired concentrations and a 2-μL droplet of this solution was deposited onto a dry PVDF membrane. The blot was air-dried for 1.5 hours, after which the membrane was activated by immersion in methanol for one minute, rinsed off, and washed with constant rocking in water and then in TTBS buffer for two minutes each. The membrane was then blocked to prevent non-specific binding with 3% BSA TTBS (w/v) for one hour at room temperature with constant rocking, and washed the PVDF membrane for two min with TTBS before finally incubating with one nM CN-PPV Pdot-streptavidin solution in 3% BSA TTBS. After incubation, the blot was washed in TTBS six times (5 minutes each) before imaging. The dot blots were imaged in TTBS on a GE Typhoon FLA 9000 Gel Imaging Scanner (GE Healthcare, Piscataway, N.J.), where a laser with 473 nm wavelength was used for excitation and a 575-nm long-pass filter was used for emission acquisition. Both Qdot and Pdot concentrations used for this experiment were 1 nM.

Figure 2:
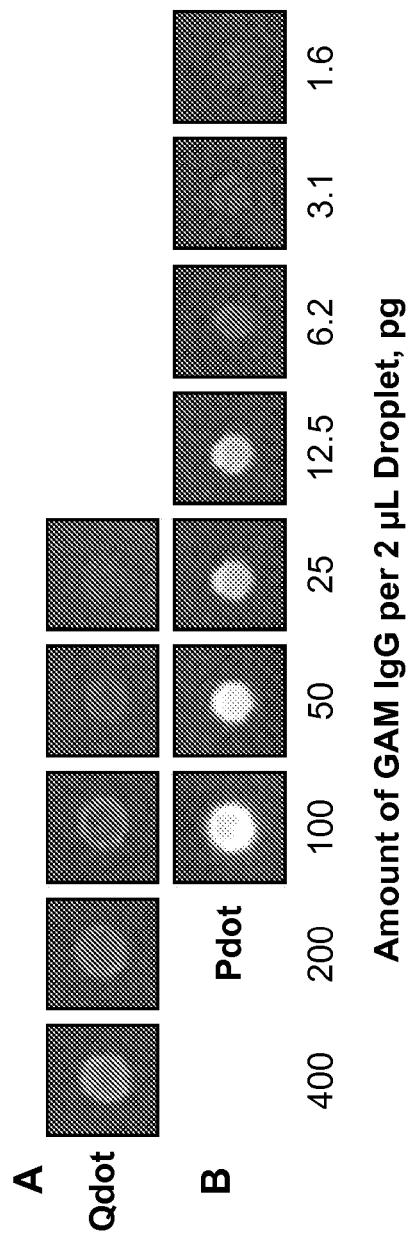
FIGS. 2A-2B show images of anti-mouse IgG-biotin dot blots incubated with Qdot 605-streptavidin (FIG. 2A) and CN-PPV Pdot-streptavidin conjugates (FIG. 2B).
FIGS. 2C and 2D show normalized integrated intensity of the corresponding dot blots shown in FIGS. 2A and 2B, respectively.
Figure 2:
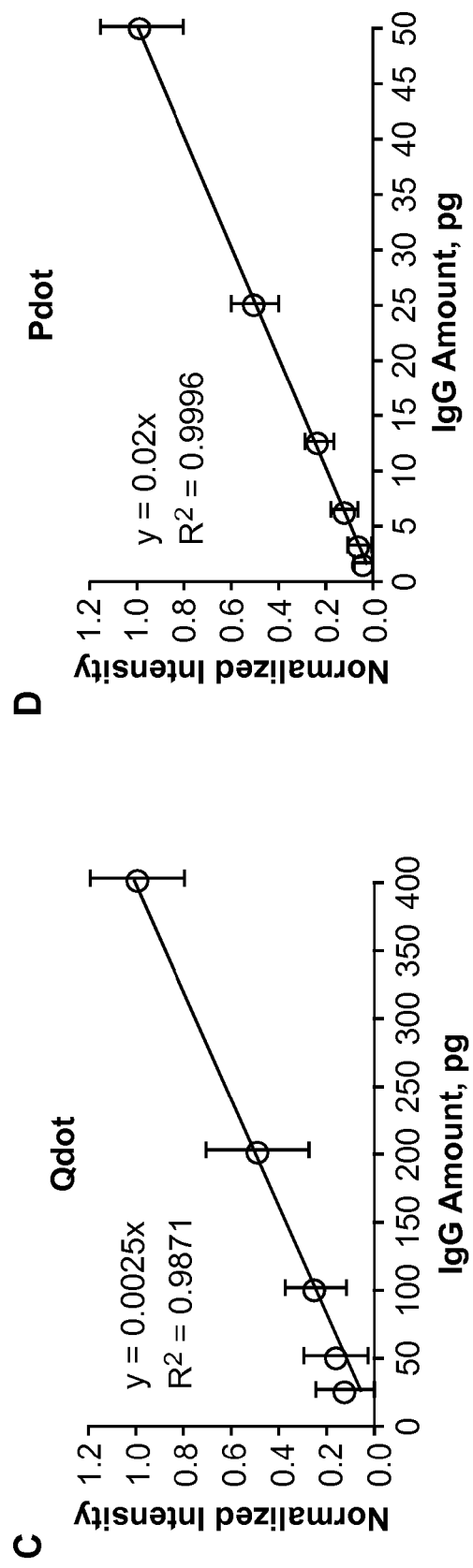

FIG. 2A shows dot blot images of GAM IgG-biotin at different concentrations incubated with Qdot 605-streptavidin. FIG. 2C shows their corresponding intensity as a function of the amount of GAM IgG. The intensity is shown in the y-axis in FIGS. 2C and 2D represents the normalized background-subtracted intensity. It can be seen that with Qdot 605-streptavidin as a fluorescent probe, a lower limit of 25 picograms of GAM IgG per two μL droplet was detected. FIG. 2B shows dot blot images of GAM IgG-biotin at different concentrations incubated with CN-PPV-streptavidin conjugates. Their corresponding intensity was a function of the amount of GAM IgG, as shown in FIG. 2D. It can be seen that with Pdot-streptavidin conjugates, the detection limit was significantly reduced to 1.6 picograms per 2-μL droplet. Thus, the detection limit of Pdot-streptavidin conjugates was an order of magnitude higher than that of Qdot-streptavidin conjugates. It should be noted that the control experiments without added GAM IgG were performed to confirm that there was not any obvious non-specific binding between Qdot/Pdot and PVDF membrane. Non-specific binding of the polymer dots can be tailored using various surface modifications (e.g., surface modification using PEG on the polymer dots) and/or using a size of polymer dots that can reduce non-specific binding.

Example 3

Use of Fluorescent Polymer Dots to Detect a Target Protein

Figure 3:
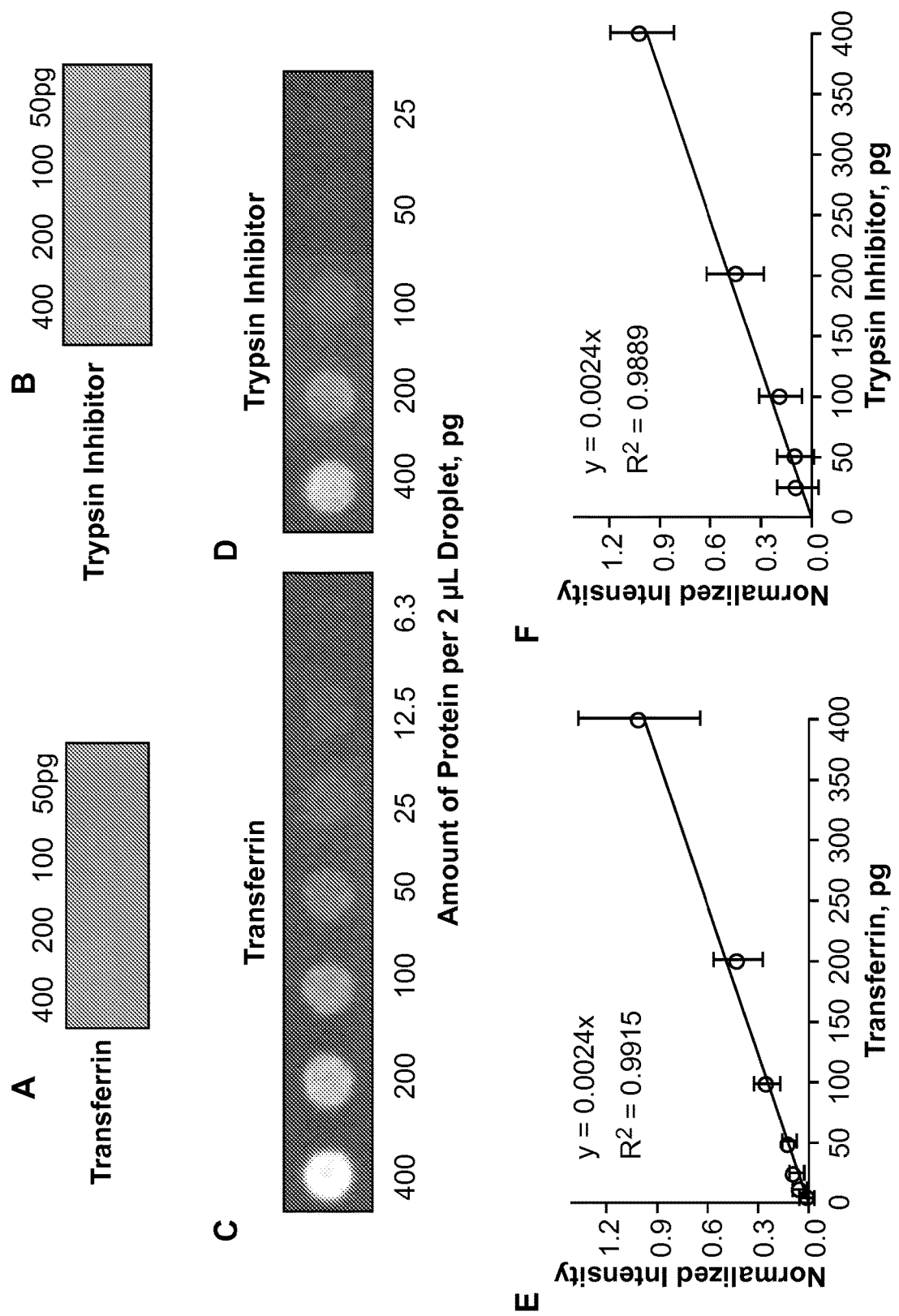
FIGS. 3A and 3B show images of (FIG. 3A) transferrin and (FIG. 3B) trypsin inhibitor dot blots without their corresponding primary antibodies. The concentration of CN-PPV Pdot-streptavidin conjugates was 1 nM. No fluorescence was detected in these dot blots, thus indicating there was no obvious non-specific binding between these Pdots and proteins.
FIGS. 3C-3F show dot blot images and the corresponding normalized background-subtracted integrated intensities of transferrin (FIGS. 3C and 3E) and trypsin inhibitor (FIGS. 3D and 3F). The dot blots were incubated with corresponding biotinylated antibodies and CN-PPV Pdot-streptavidin conjugates.

This example describes the detection of transferrin and trypsin inhibitor using fluorescently labelled CN-PPV Pdot conjugates. Next, Pdot-streptavidin conjugates were used to detect proteins in the presence of their primary antibody. Here, transferrin and trypsin inhibitor (both from Invitrogen) and their corresponding biotinylated antibodies were selected. The proteins were diluted to the desired concentrations in TTBS buffer and a 2-μL droplet of each of the solutions was deposited onto the dry PVDF membranes. Blots were air-dried for 1.5 hours, and the rest of the procedure was identical to the dot blot experiments described above in EXAMPLES 1 and 2. Specifically, the membrane was activated, washed, blocked, and then incubated with biotinylated primary antibodies (at 1:1000 dilution in TTBS) for one hour at room temperature followed by washing with TTBS five times (5 min each). The protein blots were then incubated with the CN-PPV-streptavidin Pdot solution (1 nM in 3% BSA TTBS) and the membrane is washed six times (5 minutes each) in TTBS before imaging. Different concentrations of transferrin and trypsin inhibitor were used. A control experiment without the primary antibody was performed for both proteins to determine whether there was non-specific binding between protein and Pdot-streptavidin (FIGS. 3A and 3B). The result shows that there was not any fluorescence detected from the dot blot with protein concentrations as high as 400 picograms per 2-μL droplet.

FIG. 3C shows images of the transferrin dot blots with biotinylated primary antibody and Pdot streptavidin. FIG. 3E shows the corresponding normalized background-subtracted intensity as a function of transferrin amount. A linear dependence between intensity and transferrin amount was found ($R^2$=0.9915). A detection limit of 6.3 picograms per 2-μL droplet was obtained for transferrin protein in the presence of its corresponding primary antibody.

FIG. 3D shows images of trypsin inhibitor dot blots with its biotinylated primary antibody and Pdot streptavidin. Its corresponding normalized background-subtracted intensity as a function of trypsin inhibitor was shown in FIG. 3F. A linear dependence between intensity and amount of trypsin inhibitor was also found ($R^2$=0.9889). A detection limit of 25 picograms per 2-μL droplet was obtained for trypsin inhibitor in the presence of its corresponding antibody. While not being limited to any particular theory, it is thought that the detection limit can differ between these two proteins because of the different binding efficiencies between the protein and its corresponding antibody or between the corresponding antibody and the Pdot conjugates. The variability in the number of biotin molecules per antibody unit might also have caused the difference in detection limit.

Example 4

Figure 4:
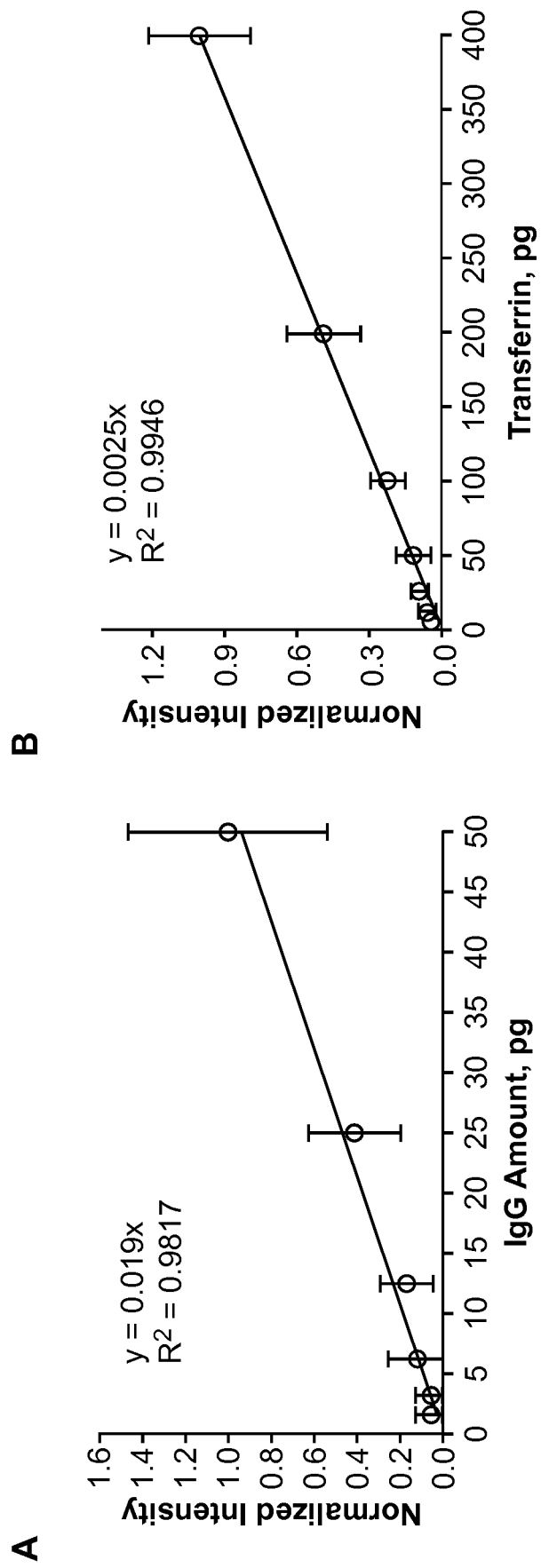
FIGS. 4A and 4B show normalized background-subtracted integrated intensity of goat anti-mouse IgG (FIG. 4A) and transferrin (FIG. 4B) dot blots incubated with corresponding biotinylated antibodies and CN-PPV Pdot-streptavidin conjugates on day 14 after incubation (samples were stored in TTBS buffer at 6° C.).

Long-Term Photo-Stability of Fluorescent Polymer Dot-Based Protein Detection This example describes the evaluation of CN-PPV Pdot conjugate photostability over time. To demonstrate the ability to repeatedly image a blot without a loss in sensitivity when using CN-PPV Pdot-streptavidin conjugates, biotinylated GAM IgG and transferrin dot blots were stored at 6° C. in TTBS buffer for up to 14 days following the labelling step. The detection limit for GAM IgG (1.6 picograms) and the linearity ($R^2$=0.9819) between intensity and amount of GAM IgG remained the same as that immediately following labelling, except for a slight increase in signal variation (FIG. 4A). The detection limit (6.3 picograms) and linearity ($R^2$=0.9946) between intensity and amount of protein for transferrin dot blot after 14 days storage at 6° C. were also found to be same as that immediately following labelling (FIG. 4B).

Example 5

Western Blot Analysis Using Fluorescent Polymer Dots

This example describes the use of Pdot-conjugates for protein visualization in a Western blotting application. A complete Western-blotting procedure was carried out and the blots were visualized with CN-PPV Pdot-streptavidin conjugates. Here, the proteins were diluted to the appropriate desired concentrations in Laemmli buffer (20% Glycerol, 2.1% SDS, 0.125 M Tris, pH 6.8, 0.73 M 2-mercaptoethanol, bromophenol blue), then the solution was heated in a 95-100° C. water bath for five minutes, cooled to room temperature and loaded onto SDS-PAGE gels (10% acrylamide for transferrin, 15% acrylamide for trypsin inhibitor, plus stacking 8% acrylamide with bromophenol blue). Fermentas PageRuler Prestained Protein Ladder (10-170 kDa) was also added as a reference. Electrophoresis was carried out at 200 V for about one hour (until the dye front ran off the gel), and the proteins were transferred from the gel to the PVDF membrane at 100 V for one hour at 6° C. The PVDF membrane was washed twice with TTBS (5 minutes each), and then the membrane was blocked and incubated in the same manner as described in the above sections. The concentration of Pdot-streptavidin conjugates was 1 nM.

Figure 5:
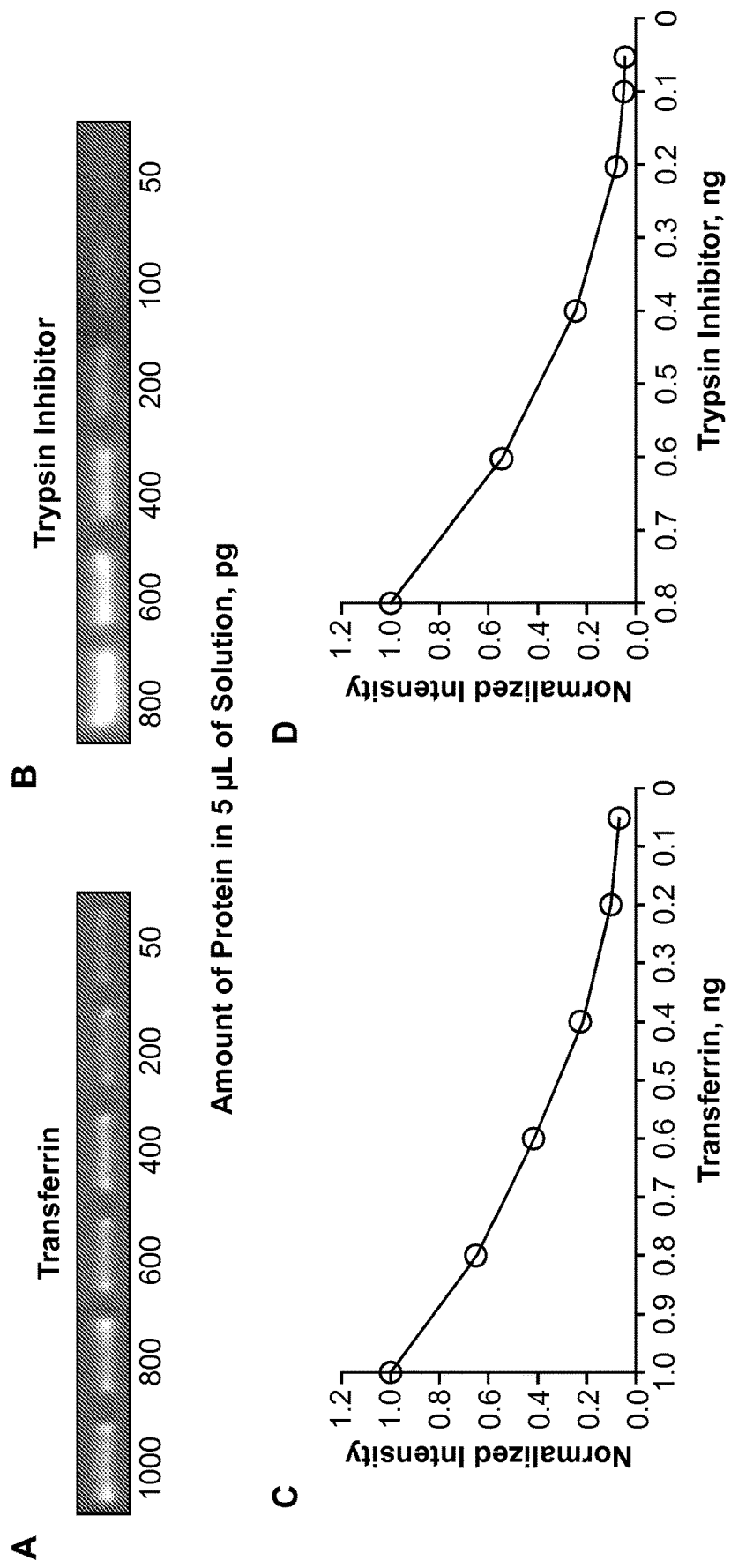
FIGS. 5A-5D show images and corresponding normalized background-subtracted integrated intensity of transferrin (FIGS. 5A and 5C) and trypsin inhibitor (FIGS. 5B and 5D) following the entire Western blotting procedure of SDS-PAGE separation, transfer to a polyvinylidene fluoride (PVDF) membrane, blocking, and incubation with corresponding biotinylated antibodies and CN-PPV Pdot-streptavidin conjugates.

FIGS. 5A and 5B show images of transferrin and trypsin inhibitor following the entire Western blotting procedure of SDS-PAGE separation, transfer to PVDF membrane, blocking, and incubation with corresponding biotinylated antibodies and CN-PPV Pdot-streptavidin conjugates. FIGS. 5C and 5D show normalized background-subtracted intensity as a function of the amount of transferrin and trypsin inhibitor, respectively. The lowest detection limit was 50 picograms for both transferrin and trypsin inhibitor. This increase in detection limit relative to the dot blots (FIG. 3) reflects the loss of some protein during their transfer from the SDS-PAGE gel to the PVDF membrane. However, it shows that Pdots are compatible with an overall Western blotting procedure and can be used to analyze samples with high detection sensitivity.

Low-picogram quantities of proteins were detected with a straightforward procedure that does not require any additional equipment or time compared to a procedure with traditional fluorescent probes. Given that Pdot emission properties can, e.g., be fine-tuned, this method can be easily extended for multiplexed detection and be widely applied for protein analysis.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A method of detecting proteins or peptides using Western blot analysis, the method comprising:
    separating the proteins or peptides from a mixture in a gel;
    transferring the separated proteins or peptides to a hydrophobic membrane;
    contacting the hydrophobic membrane having the separated proteins or peptides with a solution comprising a polymer dot conjugated to a biomolecule, wherein the polymer dot comprises a hydrophobic semiconducting polymer collapsed into a stable sub-micron-sized particle; and
    detecting at least one signal from the polymer dot, the at least one signal corresponding to the separated proteins or peptides.

2. The method of claim 1, wherein the separating the proteins or peptides comprises a chromatography method, a filtration method, a capillary electrophoresis method, a gel electrophoresis method, a liquid extraction method, a precipitation method, an immunoprecipitation method, or a combination thereof.

3. The method of claim 1, wherein the polymer dot further comprises a non-semiconducting polymer.

4. The method of claim 1, wherein the semiconducting polymer comprises a polymer selected from the group consisting of a polyfluorene polymer, a fluorene polymer, a phenylene vinylene polymer, a phenylene ethynylene polymer, a BODIPY polymer, and any derivative thereof.

5. The method of claim 1, wherein the polymer dot comprises a functional group attached to the polymer dot.

6. The method of claim 5, wherein the functional group is selected from an aldehyde, an alkene, an alkyl, an alkyne, a strained alkyne, an amino, an azido, a carbonyl, a carboxyl, a cyano, a cyclooctyne, a dieno, an ester, a succinimidyl ester, a haloalkyl, a hydroxyl, an imido, a ketone, a maleimido, a mercapto, a phosphate, a phosphine, a sulfate, a sulfonate, or a combination thereof.

7. The method of claim 1, wherein the biomolecule is a protein, a nucleic acid, a peptide, or a lipid.

8. The method of claim 7, wherein the protein is an antibody or an avidin.

9. The method of claim 1, wherein the semiconducting polymer comprises a narrow-band emissive unit.

10. The method of claim 9, wherein the narrow-band emissive unit is covalently attached to the semiconducting polymer.

11. The method of claim 9, wherein the narrow-band emissive unit comprises a BODIPY monomer, a squaraine monomer, a metal complex, a porphyrin, a phthalocyanine, a lanthanide complex, a perylene, a cyanine, a rhodamine, a couramin, a xanthene, or any derivative thereof.

12. The method of claim 4, wherein the polymer is a co-polymer.

13. The method of claim 8, wherein the antibody is a primary antibody or a secondary antibody.

14. The method of claim 5, wherein the functional group is suitable for bioconjugation.

15. The method of claim 1, wherein the hydrophobic membrane is a nitrocellulose membrane or a fluoropolymer membrane.

\* \* \* \* \*